(12) United States Patent
Matsuo et al.

(10) Patent No.: US 12,102,494 B2
(45) Date of Patent: Oct. 1, 2024

(54) BLANK FOR DENTAL CUTTING AND METHOD FOR PRODUCING SAME

(71) Applicant: TOKUYAMA DENTAL CORPORATION, Tokyo (JP)

(72) Inventors: Takuma Matsuo, Tokyo (JP); Anna Soshi, Tokyo (JP); Yuukou Nagasawa, Tokyo (JP); Hironobu Akizumi, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 542 days.

(21) Appl. No.: 17/613,419

(22) PCT Filed: May 13, 2020

(86) PCT No.: PCT/JP2020/019102
§ 371 (c)(1),
(2) Date: Nov. 22, 2021

(87) PCT Pub. No.: WO2020/235418
PCT Pub. Date: Nov. 26, 2020

(65) Prior Publication Data
US 2022/0218450 A1    Jul. 14, 2022

(30) Foreign Application Priority Data
May 22, 2019  (JP) ................. 2019-096217

(51) Int. Cl.
  *A61C 13/00*  (2006.01)
  *A61K 6/17*  (2020.01)
  *A61K 6/79*  (2020.01)
(52) U.S. Cl.
  CPC ............ *A61C 13/0022* (2013.01); *A61K 6/17* (2020.01); *A61K 6/79* (2020.01)

(58) Field of Classification Search
  None
  See application file for complete search history.

(56) References Cited

U.S. PATENT DOCUMENTS

2013/0172441 A1  7/2013  Takahata et al.
2016/0228222 A1  8/2016  Rolf et al.
(Continued)

FOREIGN PATENT DOCUMENTS

CN    108289795 A    7/2018
EP      3848418 A1    7/2021
(Continued)

OTHER PUBLICATIONS

Knarvang, Torbjørn: "Mixing of experimental composites : NIOM", NIOM Newsletter Jan. 2014, Jan. 29, 2014 (Jan. 29, 2014), XP055905279, Oslo, Norway, Retrieved from the Internet: URL:https://niom.no/mixing-of-experimental-composites/ [retrieved on Mar. 25, 2022].

(Continued)

*Primary Examiner* — Elizabeth Collister
(74) *Attorney, Agent, or Firm* — Osha Bergman Watanabe & Burton LLP

(57) ABSTRACT

Provided are a blank for dental cutting having a part to be cut made from a resin material, wherein the resin material includes a composite material in which inorganic particles are dispersed in a resin matrix, the inorganic particles are made from aggregates of inorganic spherical particles having a specific average primary particle diameter, have a narrow particle size distribution, and include one or a plurality of spherical particle groups of the same particle diameter (G-PID) having a refractive index smaller than that of the resin matrix and an ultrafine particle group (G-SFP), and the arrangement structure of all of the inorganic spherical particles constituting the spherical particle groups of the same particle diameter in the resin matrix has a short-range (Continued)

ordered structure that fulfills specific conditions, and a method for producing the same.

9 Claims, 5 Drawing Sheets

(56) References Cited

U.S. PATENT DOCUMENTS

| | | | |
|---|---|---|---|
| 2018/0303721 A1 | 10/2018 | Akizumi et al. | |
| 2019/0292278 A1 | 9/2019 | Akizumi et al. | |
| 2020/0121564 A1 | 4/2020 | Matsuo et al. | |
| 2020/0129384 A1 | 4/2020 | Morisaki et al. | |
| 2020/0237487 A1* | 7/2020 | Inoue | A61C 13/082 |
| 2021/0095113 A1 | 4/2021 | Matsuo et al. | |

FOREIGN PATENT DOCUMENTS

| | | |
|---|---|---|
| JP | H09-255516 A | 9/1997 |
| JP | 2012-153640 A | 8/2012 |
| JP | 5274164 B2 | 8/2013 |
| JP | 2016-535610 A | 11/2016 |
| JP | 2017-213394 A | 12/2017 |
| RU | 2557961 C2 | 7/2015 |
| WO | 2011087832 A1 | 7/2011 |
| WO | 2012/042911 A1 | 4/2012 |
| WO | 2015/051095 A1 | 4/2015 |
| WO | 2017/069274 A1 | 4/2017 |
| WO | 2018101236 A1 | 6/2018 |
| WO | 2018/194031 A1 | 10/2018 |
| WO | 2018/194032 A1 | 10/2018 |
| WO | 2019/189698 A1 | 10/2019 |
| WO | 2020/050123 A1 | 3/2020 |

OTHER PUBLICATIONS

International Search Report issued in corresponding international application No. PCT/JP2020/019102, dated Jun. 23, 2020 (3 pages).
Written Opinion of the International Searching Authority issued in corresponding international application No. PCT/JP2020/019102, dated Jun. 12, 2020 (4 pages).

* cited by examiner

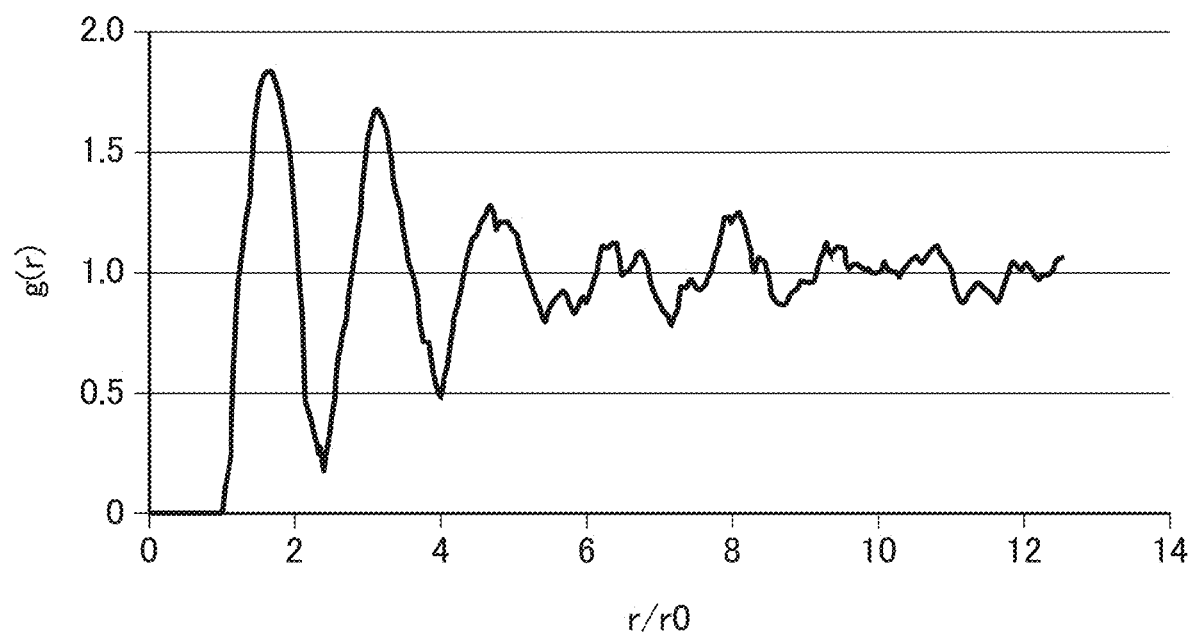

BLANK FOR DENTAL CUTTING AND METHOD FOR PRODUCING SAME

TECHNICAL FIELD

The present invention relates to a dental mill blank including a composite material containing a resin matrix and inorganic particles dispersed in the resin matrix, and also relates to a method of producing such a blank. Specifically, the present invention relates to a dental mill blank that has a structural color and a suitable level of contrast ratio to make it possible to form dental prostheses with colors highly conformable with different colors of natural teeth without particular use of pigments or dyes, and also relates to a method of producing such a blank.

BACKGROUND ART

In dental treatment, digital technologies have become more frequently used for forming dental prostheses, such as inlays, onlays, crowns, bridges, and implant superstructures. For example, as disclosed in Patent Document 1, a computer aided design (CAD)-computer aided manufacturing (CAM) system has become more frequently used, which employs oral cavity images to perform milling on a dental mill blank of a non-metallic material using a CAD-CAM device based on CAD-CAM technology. As used herein, the term "dental mill blank" refers to a material that is attachable to a milling machine in a CAD-CAM system and to be subjected to milling (also called "mill blank"). Generally known dental mill blanks include (solid) blocks having a rectangular shape, a cylindrical shape, or any other shape and (solid) disks having a plate or disk shape. A fastening pin is often joined to a dental mill blank so that the blank can be fixed to a milling machine. Such a form integrated with a fastening pin is also called a dental mill blank. As used herein, the term "dental mill blank" also includes such a form integrated with a fastening pin. The material main body to be subjected to milling (the main body of a dental mill blank) is also referred to as "milling target portion".

The milling target portion of a dental mill blank may be made of any of various materials, such as glass ceramics, zirconia, titanium, and resins. Among them, a resin-based material composed of a cured product of a curable composition containing an inorganic filler, such as silica, a polymerizable monomer, such as a methacrylate resin, and a polymerization initiator has attracted attention in terms of high workability (milling workability), high aesthetics, strength, and other properties.

Dental treatment requires providing an appearance with a color as close to that of natural teeth as possible. Proposals to meet such an aesthetic requirement include a single-component, monolayer-structure, dental mill blank, which has a color adjusted by addition of a suitably selected type and amount of a pigment or dye; and a multilayer-structure, dental mill blank, which has a stack of component layers with different colors.

For example, Patent Document 2 discloses a dental mill blank having high versatility, high productivity, and high ability to reproduce the beauty of natural teeth, which is a dental CAD-CAM-purpose resin-based block having a stack of a dentin restorative resin layer and an enamel restorative resin layer, in which at least the dentin restorative resin layer contains light diffusing particles and provides a specific diffusion ratio.

Patent Document 1: Japanese Unexamined Patent Application (Translation of PCT Application), Publication No. 2016-535610
Patent Document 2: Japanese Unexamined Patent Application, Publication No. 2017-213394
Patent Document 3: Japanese Patent No. 5274164
Patent Document 4: PCT International Publication No. WO2017/069274

DISCLOSURE OF THE INVENTION

Problems to be Solved by the Invention

Unfortunately, a dental prosthesis produced from a dental mill blank containing a color-adjusting pigment or dye may suffer from aging deterioration-induced discoloration or color degradation of the pigment or dye, so that the appearance of the restored portion may change in color and become unconformable with that of the natural teeth as time goes by after the restoration.

It is therefore an object of the present invention to provide a resin-based material-containing, dental mill blank less vulnerable to such a problem and to provide a method of producing such a blank.

Means for Solving the Problems

A first aspect of the present invention relates to a dental mill blank, having a milling target portion including a resin-based material,
the resin-based material including at least one composite material containing a resin matrix and inorganic particles dispersed in the resin matrix,
the inorganic particles including:
at least one group of identical diameter spherical particles (G-PID) including spherical inorganic particles with a specific average primary particle diameter in the range of 100 nm to 1,000 nm and having a number-size distribution in which 90% or more of all particles have particle diameters falling within the range of the average primary particle diameter−5% of the average primary particle diameter to the average primary particle diameter+5% of the average primary particle diameter; and
a group of superfine particles (G-SFP) including inorganic particles with an average primary particle diameter of less than 100 nm,
the at least one group including one or more groups of identical diameter spherical particles, wherein
the one or more groups of identical diameter spherical particles are A groups each represented by $G\text{-}PID_m$, wherein A is the number of the groups, m is 1 where A is 1 or m is a positive integer of 1 to A where A is 2 or more, and the average primary particle diameter of the group increases with increasing m,
the groups represented by $G\text{-}PID_m$ have average primary particle diameters differing by 25 nm or more from each other, the group of superfine particles has an average primary particle diameter 25 nm or more smaller than that of the group represented by $G\text{-}PID_1$,
the at least one composite material satisfies the relation $n_{(Mx)} < n_{(G\text{-}PIDm)}$, wherein $n_{(Mx)}$ is the refractive index of the resin matrix for light with a wavelength of 589 nm at 25° C., $n_{(G\text{-}PIDm)}$ is the refractive index of the spherical inorganic particles of each group represented by $G\text{-}PID_m$ for light with a wavelength of 589 nm at 25° C., and the relation is satisfied for each $n_{(G\text{-}PIDm)}$, and the at least one composite material has a short-range order structure in which the spherical inorganic particles of all the groups of identical diameter spherical particles in the resin matrix have an arrangement structure satisfying:

Condition 1 where a radial distribution function graph plotted with $r/r_0$ on the x axis and a radial distribution function $g(r)$ on the y axis and showing the relationship between $r/r_0$ and the $g(r)$ for r, wherein $r/r_0$ is a normalized dimensionless number calculated by dividing a distance r from the center of any spherical inorganic particle in the composite material by the average particle diameter $r_0$ of all spherical inorganic particles dispersed in the composite material and the $g(r)$ represents the probability of existence of any other spherical inorganic particle at a point apart by the distance r from the center of the any spherical inorganic particle, has peaks among which the peak closest to the origin provides a distance $r_1$ between nearest neighbor particles as the r value corresponding to the top of the peak, and the distance $r_1$ between nearest neighbor particles is 1 to 2 times the average particle diameter $r_0$ of all spherical inorganic particles dispersed in the composite material; and Condition 2 where the radial distribution function graph has peaks among which the peak second closest to the origin provides a distance $r_2$ between second nearest neighbor particles as the r value corresponding to the top of the peak, and the radial distribution function $g(r)$ has a local minimum value of 0.56 to 1.10 between the distance $r_1$ between nearest neighbor particles and the distance $r_2$ between second nearest neighbor particles.

In the dental mill blank according to the present invention, the radial distribution function $g(r)$ is preferably calculated from Formula (1): $g(r) = \{1/<\rho>\} \times \{dn/da\}$, wherein $<\rho>$ is the average density of the spherical inorganic particles in an observation plane that is an interior surface of the composite material, wherein the average density is determined from a scanning electron microscopy image of the interior surface of the composite material, do is the number of spherical inorganic particles in a region between a circle with a circumference apart by the distance r from any spherical inorganic particle in the observation plane and a circle with a circumference apart by the distance r+dr from the any spherical inorganic particle, and da is the area of the region, wherein $da = 2\pi r \times dr$.

In the dental mill blank according to the present invention, the total amount of the group or groups of identical diameter spherical particles dispersed in the resin matrix is preferably 10 parts by mass to 1,500 parts by mass based on 100 parts by mass of the resin matrix, and the amount of the group of superfine particles dispersed in the resin matrix is preferably 0.1 parts by mass to 50 parts by mass based on 100 parts by mass of the resin matrix, all the group or groups of identical diameter spherical particles in the inorganic particles preferably have an average primary particle diameter in the range of 230 nm to 1,000 nm, and the group of superfine particles preferably has an average primary particle diameter in the range of 3 nm to 75 nm, in view of block color and contrast ratio. Moreover, the difference between $n_{(Mx)}$ and $n_{(G-PIDm)}$ ($n_{(G-PIDm)} - n_{(MX)}$), which is represented by $\Delta n$, is preferably 0.001 to 0.1 for each $n_{(G-PIDm)}$.

In the dental mill blank, the at least one composite material in the milling target portion may include multiple composite materials having different compositions and being bonded together.

A second aspect of the present invention relates to a method of producing the dental mill blank of the present invention having a milling target portion in a specific shape, the method including:

mixing a polymerizable monomer component (A), inorganic particles (B), and a polymerization initiator (C) to form a polymerizable curable composition, the polymerizable monomer component (A) being capable of forming a cured product having a refractive index of 1.40 to 1.57 for light with a wavelength of 589 nm at 25° C., the inorganic particles (B) including: the group of identical diameter spherical particles including a material having a refractive index higher than that of the cured product made from the polymerizable monomer component (A) for light with a wavelength of 589 nm at 25° C.; and the group of superfine particles; and subjecting the polymerizable curable composition to cast molding and polymerization to form a composite material bulk body that forms the whole or part of the milling target portion, wherein the mixing is carried out so as to form a polymerizable curable composition capable of forming a cured product containing spherical inorganic particles that form all the group or groups of identical diameter spherical particles and have a short-range order structure satisfying the Conditions 1 and 2 as an arrangement structure.

In the production method according to the present invention, at least some of the group or groups of identical diameter spherical particles in the polymerizable curable composition are preferably in the form of an organic-inorganic composite filler including: one group of identical diameter spherical particles; and a resin having a refractive index lower than that of spherical inorganic particles of the one group of identical diameter spherical particles for light with a wavelength of 589 nm at 25° C. and being free of any group of identical diameter spherical particles other than the one group of identical diameter spherical particles, so that the short-range order structure can be reliably obtained.

Moreover, for uniform polymerization and curing, the polymerization initiator (C) is preferably a thermal polymerization initiator, and the cast molding and polymerization are preferably carried out at 60° C. to 200° C.

Effects of the Invention

The dental mill blank according to the present invention brings about the following advantageous effects: (a) it does not need to include a dye or pigment and thus is less vulnerable to the problem of long-term discoloration; (b) it can have a desired color within a wide color range from a blue transparent color to a color of yellow to red which is the same as that of the dentin; and (c) the group of superfine particles (G-SFP) in it provides a suitable level of transparency so that it can form a relatively thick dental prosthesis with a color easily conformable with that of the tooth to be restored and allows teeth with a wide range of colors to be restored with an appearance close to that of natural teeth. When the dental mill blank contains multiple groups of identical diameter spherical particles (G-PID), each G-PID provides a structural color depending on the average primary particle diameter, and therefore, the combination of the groups (G-PID) makes it possible to control the coloring of the entire blank.

In the dental mill blank according to the present invention, the state of dispersion of the spherical filler in the resin matrix of the composite material as a part or the whole of the milling target portion can be checked by electron microscope observation. Therefore, the inspection of the correlation between the dispersion state and the production conditions, such as conditions for mixing to form the polymerizable curable composition as a raw material, makes it possible to determine production conditions under which the advantageous effects can be reliably produced. The production method of the present invention using such conditions allows high-yield production of the dental mill blank of the present invention.

BRIEF DESCRIPTION OF THE DRAWINGS

FIG. 8 is a graph showing a radial distribution function with respect to a piece of a cured product cut from the dental mill blank of Comparative Example 2.

PREFERRED MODE FOR CARRYING OUT THE INVENTION

Figure 1A:
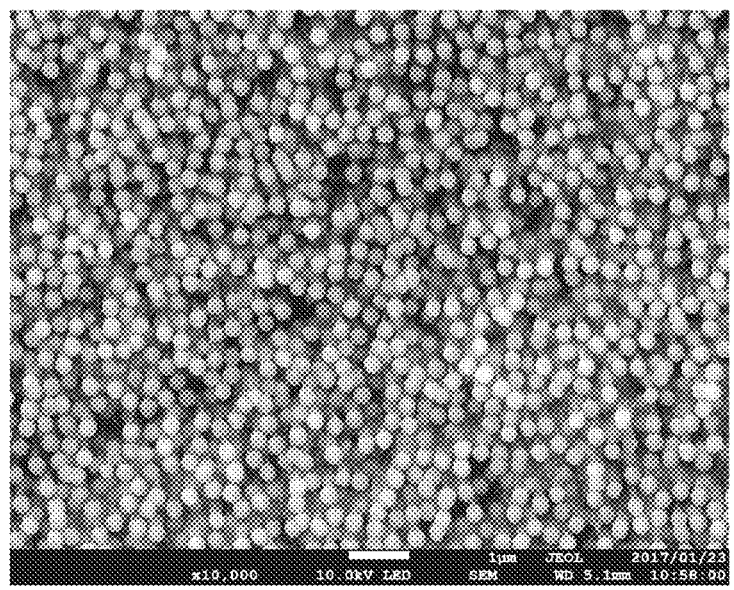
FIG. 1A is a view showing an example of an image of a plane of a piece of a cured product cut from the dental mill blank of Example 1, which is observed with a scanning electron microscope.

The dental mill blank according to the present disclosure has a milling target portion including a resin-based material, in which the resin-based material includes a specific composite material containing a resin matrix and inorganic particles dispersed in the resin matrix. Specifically, the whole of the milling target portion includes the specific composite material, or a part of the milling target portion includes the specific composite material and the remaining part of it includes another resin-based material. The part including the specific composite material may include multiple specific composite materials having different compositions and joined together.

The specific composite material contains a resin matrix and specific inorganic particles that are dispersed in the resin matrix so as to satisfy specific dispersion conditions. Without containing any specific pigment or dye, the specific composite material provides (produces) a color based on a coloration mechanism which is what is called "structural color". The term "structural color" means a color produced when fine particles in a medium cause reflection, interference, scattering, and transmission of light. Known techniques use a composite material to produce a desired color, in which the composite material contains inorganic particles dispersed in a medium such as a resin (see Patent Documents 3 and 4).

For example, Patent Document 3 discloses a fine particle dispersion including first fine particles that are dispersed in a medium and have an average particle diameter in the range of 50 nm to 1 μm and a particle diameter Cv of 10% or less, in which the first fine particles are arranged to have an amorphous structure, the fine particle dispersion having a short-range order structure satisfying specific conditions defined by an in-plane radial distribution function g(r). Patent Document 3 discloses that such a fine particle dispersion stably maintains the fine particle arrangement structure and can reflect light with a specific wavelength and sufficiently reduce the angle dependence of reflected light having a peak wavelength varying with the incident angle of light.

Patent Document 4 discloses a curable composition containing a polymerizable monomer component (A), a spherical filler (B) including particles having an average particle diameter in the range of 230 nm to 1,000 nm, and a polymerization initiator (C), the curable composition satisfying conditions where 90% or more of the particles have particle diameters falling within the range of the average particle diameter−5% of the average particle diameter to the average particle diameter+5% of the average particle diameter, and at 25° C., the spherical filler (B) has a refractive index $n_F$ larger than that of a polymerization reaction product of the polymerizable monomer component (A), the curable composition being capable of forming a cured product with a thickness of 1 mm that has a value (V) of less than 5 and a chroma (C) of 0.05 or more in the Munsell color system as measured for colored light on a black background with a color-difference meter and has a value (V) of 6 or more and a chroma (C) of less than 2 in the Munsell color system as measured for colored light on a white background with a color-difference meter.

Patent Document 4 states that a dental composite resin (CR) made from the curable composition has the following advantageous features: (1) it hardly causes the problem of discoloration over time since it contains no dye or piment; (2) it can form a cured product with a color of yellow to red, which is the same as that of the dentin; and (3) the cured product has a suitable level of transparency and thus has a color easily conformable with that of the tooth to be restored, so that only a single type of composite resin can be used to restore teeth with a wide range of colors to produce an appearance close to that of natural teeth without complicated shade taking or selection of composite resin shade.

Patent Document 3 suggests that fine particles with homogeneous particle diameters dispersed to have a specific short-range order structure and to have an amorphous structure as a whole can produce a constant structural color not dependent on changes in the incident angle of light. Patent Document 4 also shows that the cured product of the curable composition (or the CR made from the curable composition) has a portion with the component particles gathered in a relatively regular fashion, which causes interference for production of colored light, and also has a portion with the component particles dispersed in an unregulated fashion, which causes scattering for production of colored light. This may suggest that, in such a system, the balance between long-range irregularity and short-range regularity in the state of dispersion of the spherical filler is important for the advantages (1) to (3) mentioned above.

However, Patent Document 4 discloses nothing about quantitative evaluation of the balance for the advantageous effects with respect to the curable composition. For example, it remains unknown how the advantageous effects are affected when a fine filler is added to adjust the viscosity of the curable composition or to adjust the contrast ratio of the cured product. Regarding the spherical filler (B), Patent Document 4 only discloses use of a single group of spherical inorganic particles having a specific average primary particle diameter in the range of 230 nm to 1,000 nm and having a number-size distribution in which 90% or more of all particles have particle diameters falling within the range of the average primary particle diameter−5% of the average primary particle diameter to the average primary particle diameter+5% of the average primary particle diameter. Therefore, it remains unknown how the advantageous effects are affected when multiple groups of such particles with different average primary particle diameters are used. Moreover, the disclosure in Patent Document 4 is mainly intended to restore so-called shallow cavities with CR, and therefore, it remains unknown whether the same advantageous effect can be obtained when a thick dental prosthesis is formed. Furthermore, it has been found that desired advantageous effects cannot be obtained depending on the conditions for the preparation of the curable composition by mixing of components although the frequency of such a problem is not so high.

The unknown conditions mentioned above and variations in the practical physical properties dependent on the conditions for the preparation of the curable composition may also be problems not only when the curable composition is used for CR but also when a cured product of the composition is used as a dental prosthesis.

The present inventors utilized a method of defining a short-range order structure based the "in-plane radial distribution function g(r)" disclosed in Patent Document 3 in order to quantify the state of dispersion of spherical particles. Based on such a method, the present inventors specified the state of dispersion of inorganic particles for producing the advantageous effects with respect to a system containing a resin matrix and inorganic particles including a group of identical diameter spherical particles (G-PID) and a group of superfine particles (G-SFP), dispersed in the resin matrix, which is similar to that disclosed in Patent Document 4. As a result, the present inventors have made a dental mill blank using a composite material having the specified state of dispersion, from which the unknown conditions and variations in practical physical properties are eliminated.

The present inventors have already proposed such a composite material (Japanese Patent Application No. 2018-165680). The present invention has been made based on findings that the short-range order structure of the composite material according to the proposal (also referred to as the "composite material of the present disclosure") for producing the advantageous effects can be successfully defined (in other words, the advantageous effects can be obtained when Conditions 1 and 2 defined above are satisfied) in a system similar to that disclosed in Patent Document 4; addition of a superfine inorganic filler has almost no effect on the structural color production mechanism; and as long as the specific conditions are satisfied, multiple groups of spherical fillers may be used, and even in such a case, the short-range order structure is maintained to allow each group of spherical fillers to produce a structural color, and the structural colors produced by the groups are combined to give a certain structural color as a whole. The composite material of the present disclosure differs from the composite material disclosed in Patent Document 4 in that the cured product of Patent Document 4 contains only a single group of identical diameter spherical particles (G-PID) with an average particle diameter in the range of 230 nm to 1,000 nm and does not contain any specific group of superfine particles (G-SFP), whereas the composite material of the present disclosure contains one or more groups of identical diameter spherical particles (G-PID) with an average particle diameter in the range of 100 nm to 1,000 nm and also contains a group of superfine particles (G-SFP) for the purpose of adjusting the contrast ratio of the cured product.

Moreover, the present invention has been made based on new findings that, also when formed with a large thickness, such as 10 mm, the composite material of the present disclosure can also produce the advantageous effects and thus is suitable for use as a dental mill blank, as well as based on the findings about the composite material of the present disclosure.

Hereinafter, the present invention will be described in detail including the composite material of the present disclosure.

The composite material of the present disclosure constituting the dental mill blank of the present disclosure contains a resin matrix and inorganic particles dispersed in the resin matrix and has the features described below.

First, the inorganic particles include at least one group (or one or more groups) of identical diameter spherical particles (G-PID) including spherical inorganic particles with an average primary particle diameter in the range of 100 nm to 1,000 nm and having a number-size distribution in which 90% or more of all particles have particle diameters falling within the range of the average primary particle diameter−5% of the average primary particle diameter to the average primary particle diameter+5% of the average primary particle diameter; and a group of superfine particles (G-SFP) including inorganic particles with an average primary particle diameter of less than 100 nm.

Second, the one or more groups of identical diameter spherical particles are A groups each represented by G-PID$_m$, wherein A is the number of the groups, m is 1 where A is 1 or m is a positive integer of 1 to A where A is 2 or more, and the average primary particle diameter of the group increases with increasing m, the groups represented by G-PID$_m$ have average primary particle diameters differing by 25 nm or more from each other, and the group of superfine particles has an average primary particle diameter that is 25 nm or more smaller than that of the group represented by G-PID$_1$.

Third, the composite material satisfies the relation $n_{(Mx)} < n_{(G-PIDm)}$, wherein $n_{(Mx)}$ is the refractive index of the resin matrix for light with a wavelength of 589 nm at 25° C., $n_{(G-PIDm)}$ is the refractive index of the spherical inorganic particles of each group represented by G-PID$_m$ for light with a wavelength of 589 nm at 25° C., and the relation is satisfied for each $n_{(G-PIDm)}$.

Fourth, the composite material has a short-range order structure in which the spherical inorganic particles of all the groups of identical diameter spherical particles in the resin matrix have an arrangement structure satisfying Conditions 1 and 2 below.

Condition 1: A radial distribution function graph plotted with $r/r_0$ on the x axis and a radial distribution function g(r) on the y axis and showing the relationship between $r/r_0$ and the g(r) for r, wherein $r/r_0$ is a normalized dimensionless number calculated by dividing a distance r from the center of any spherical inorganic particle in the composite material by the average particle diameter $r_0$ of all spherical inorganic particles dispersed in the composite material and the g(r) represents the probability of existence of any other spherical inorganic particle at a point apart by the distance r from the center of the any spherical inorganic particle, has peaks among which the peak closest to the origin provides a distance $r_1$ between nearest neighbor particles as the r value corresponding to the top of the peak, and the distance $r_1$ between nearest neighbor particles is 1 to 2 times the average particle diameter $r_0$ of all spherical inorganic particles dispersed in the composite material.

Condition 2: The radial distribution function graph has peaks among which the peak second closest to the origin provides a distance $r_2$ between second nearest neighbor particles as the r value corresponding to the top of the peak, and the radial distribution function g(r) has a local minimum value of 0.56 to 1.10 between the distance $r_1$ between nearest neighbor particles and the distance $r_2$ between second nearest neighbor particles.

The composite material of the present disclosure having all of the four features allows incident light to undergo diffraction and interference according to the Bragg condition so that light with a specific wavelength is strengthened without being affected by the incident angle of light to produce a structural color according to the average primary particle diameter, which results in production of a specific structural color according to the average primary particle diameter.

As mentioned above, the composite material of the present disclosure basically falls within a category the same as that of the cured product of the curable composition disclosed in Patent Document 4. However, the composite material of the present disclosure has the following new features: it has the specified state of dispersion of spherical inorganic particles, which reliably produces the advantageous effects; it contains an additional inorganic filler with particles sizes having no adverse effect on the advantageous effects, which corresponds to one of "optional additives" for the curable composition disclosed in Patent Document 4; and it may contain multiple groups of identical diameter spherical particles. The composite material of the present disclosure may have other features similar to those of the curable composition disclosed in Patent Document 4, such as the polymerizable monomer component as a raw material for the resin matrix and the type of each group of identical diameter spherical particles, more specifically, the average primary particle diameter and number-size distribution of the G-PID, the shape, material, and refractive index of spherical inorganic particles in the G-PID, and the polymerization initiator used to form the cured product.

Therefore, first, the fourth feature regarding the specified state of dispersion of spherical inorganic particles will be described, and then what raw materials and what methods should be used to form the composite material of the present disclosure will be described.

The state of dispersion of spherical inorganic particles in the composite material of the present disclosure is quantified by a method of defining a short-range order structure using the "in-plane radial distribution function g(r)" disclosed in Patent Document 3. The radial distribution function g(r) is a well-known function for determining the probability of existence of a particle at a point apart by a distance r from any other particle, as shown also in Patent Document 3. The radial distribution function g(r) is defined by Formula (1) below.

$$g(r) = \{1 / <\rho>\} \times \{dn/da\} \quad (1)$$

In Formula (1), $<\rho>$ represents the average density of in-plane particles, do represents the number of particles in a region between a circle with a circumference apart by the distance r from any in-plane particle at a center and a circle with a circumference apart by the distance r+dr from the any spherical inorganic particle, and da represents the area of the region, wherein da=2πr×dr.

In general, the radial distribution function g(r) is expressed by a radial distribution function graph plotted with distance r on the x axis (distance axis) and g(r) (the result of calculation from Formula (1)) for r on the y axis or expressed by a radial distribution function graph plotted with a normalized dimensionless number calculated by dividing r by the average particle diameter on the distance axis and with the g(r) value (the result of calculation from the formula) for r corresponding to the x axis value on the y axis (vertical axis) (see FIGS. 2 to 8).

Regarding the composite material of the present disclosure, $<\rho>$ and dn can be easily and reliably determined. Therefore, the g(r) is preferably calculated from Formula (1) based on $<\rho>$ and dn, which are determined from a scanning electron microscopy image of an interior surface of the composite material of the present disclosure in the observation plane, and da (=2πr×dr), which corresponds to the dr value used for the determination of dn.

The $<\rho>$, dn, and da may be determined as shown below. First, the composite material of the present disclosure is prepared by subjecting a polymerizable curable composition as a raw material (also referred to as the "polymerizable curable composition of the present disclosure") to curing and other processes, and the resulting composite material is subjected to surface polishing or other working so that a plane in which the state of dispersion of spherical inorganic particles in the composite material is observable (observation plane) is exposed at the surface. Then, the observation plane is observed with a scanning electron microscope, and a microscopic image of a region containing at least 500 spherical inorganic particles is taken in the plane. The resulting scanning electron microscopy image is then analyzed using image analysis software (e.g., Simple Digitizer ver. 3.2 (free software)) so that the coordinates of spherical inorganic particles in the region are determined. The coordinates of any one of the spherical organic particles are selected from the coordinate data. A circle with a radius equal to the distance r is drawn with the selected spherical inorganic particle at the center to contain at least 200 spherical inorganic particles. The number of the spherical inorganic particles within the circle is counted and used to determine the average particle density $<\rho>$ (in units of counts per $cm^2$).

The do may be determined by setting dr to about $r_0/100$ to about $r_0/10$, wherein $r_0$ represents the average particle diameter of the spherical inorganic particles, drawing another circle that is concentric with the circle of the radius r and has a radius of r+dr, and counting the number of spherical inorganic particles in the region between the two circles. The da, which is the area of the region between the two circles, is determined to be 2πr·dr based on the actually set length dr.

The composite material of the present disclosure needs to be such that a radial distribution function graph plotted with $r/r_0$ on the x axis and a radial distribution function g(r) on the y axis and showing the relationship between $r/r_0$ and the g(r)

for r, wherein $r/r_0$ is a normalized dimensionless number calculated by dividing the distance r from the center of any spherical inorganic particle in the composite material by the average particle diameter $r_0$ of all spherical inorganic particles dispersed in the composite material and the g(r) represents the probability of existence of any other spherical inorganic particle at a point apart by the distance r from the center of the any spherical inorganic particle, has peaks among which the peak closest to the origin provides a distance $r_1$ between nearest neighbor particles as the r value corresponding to the top of the peak, and the distance $r_1$ between nearest neighbor particles is 1 to 2 times the average particle diameter $r_0$ of all spherical inorganic particles dispersed in the composite material (Condition 1). If $r_1$ is less than 1 time $r_0$ ($r_1/r_0<1$), many particles will overlap each other in the plane, so that a structural color may fail to be produced. If $r_1$ is more than 2 times $r^0$ ($r_1/r_0>2$), a structural color may fail to be produced because no particle will exist near the selected central inorganic particle so that the short-range order will be lost. Therefore, $r_1/r_0$ should be 1.0 to 2.0, preferably 1.0 to 1.5, in order to maintain the short-range order and to facilitate the production of a structural color.

The composite material of the present disclosure also needs to be such that the radial distribution function graph has peaks among which the peak second closest to the origin provides a distance $r_2$ between second nearest neighbor particles as the r value corresponding to the top of the peak, and the radial distribution function g(r) has a local minimum value of 0.56 to 1.10 between the distance $r_1$ between nearest neighbor particles and the distance $r_2$ between second nearest neighbor particles (Condition 2). If the local minimum value is less than 0.56, the spherical inorganic particles will have an arrangement structure with a high long-range order, which will increase not only the light incidence angle-dependence of the produced structural color but also the chroma of the composite material, so that the composite material will be less likely to have color conformity when used as a dental filling material. On the other hand, if the local minimum value exceeds 1.10, the spherical inorganic particles will have a random arrangement structure so that the desired reflection performance will be difficult to obtain and the desired structural color will be difficult to produce. Therefore, the local minimum value should be 0.56 to 1.10, preferably 0.56 to 1.00, in order to facilitate producing a structural color and providing color conformity for the dental filling material.

As a result of studies, the present inventors have found that the curable composition disclosed in Patent Document 4 fails to produce the desired advantageous effects depending on the conditions for the preparation of the composition (CR) by mixing of components although the frequency of such a problem is very low and that such a system that fails to produce the advantageous effects does not satisfy Condition 1 and/or Condition 2 as a result of evaluation of the radial distribution function g(r) of the system. This means that the arrangement structure of spherical inorganic particles in the group of identical diameter particles in the composite material of the present disclosure correlates with production conditions, such as conditions for kneading the raw materials. Specifically, if kneading is performed under conditions that can easily cause unevenness, such as manual kneading, insufficient kneading conditions may occur with a certain probability, so that Condition 1 or 2 may fail to be satisfied, which may result in failure to obtain the desired color conformity and result in a reduction in production yield. On the other hand, Conditions 1 and 2 are reliably satisfied using appropriate measures, such as kneading under controlled conditions by means of a kneading machine and degassing to prevent the composite material from containing air bubbles.

Next, raw materials for the composite material of the present disclosure, production methods, and other conditions will be described.

<Polymerizable Monomer Component (A)>

The polymerizable monomer component (A), which is preferably used to form the resin matrix, may be, but not limited to, one or more selected from radically polymerizable monomers, such as (meth)acrylic compounds; and cationically polymerizable monomers, such as epoxies and oxetanes, and so on. A (meth)acrylic compound is preferably used to form a dental polymerizable curable composition. Such a (meth)acrylic compound may be any of a monofunctional polymerizable monomer and a polyfunctional polymerizable monomer, as disclosed in Patent Document 4. Such a (meth)acrylic compound may have an acidic group or a hydroxy group in the molecule or may be aromatic or aliphatic. Examples of the (meth)acrylic compound, which is preferably used to form a dental polymerizable curable composition, include methyl(meth)acrylate, ethyl (meth) acrylate, 2-ethylhexyl(meth)acrylate, (meth)acrylic acid, N-(meth)acryloylglycine, p-vinylbenzoic acid, 2-(meth) acryloyloxybenzoic acid, 6-(meth)acryloyloxyethylnaphthalene-1,2,6-tricarboxylic anhydride, 13-(meth)acryloyloxytridecane-1,1-dicarboxylic acid, 2-(meth)acrylamido-2-methylpropanesulfonic acid, 2-hydroxyethyl(meth)acrylate, 3-hydroxypropyl(meth)acrylate, N-hydroxyethyl(meth) acrylamide, N,N-(dihydroxyethyl)(meth)acrylamide, 2,2-bis ((meth)acryloyloxyphenyl)propane, 2,2-bis[(3-(meth)acryloyloxy-2-hydroxypropyloxy)phenyl]propane, ethylene glycol di(meth)acrylate, triethylene glycol di(meth)acrylate, 1,6-bis((meth)acrylethyloxycarbonylamino)trimethyl-hexane, trimethylolpropane tri(meth)acrylate, pentaerythritol tetra(meth)acrylate, and neopentylglycol di(meth)acrylate.

If necessary, two or more of these (meth)acrylic polymerizable monomers may be used in combination.

In general, multiple polymerizable monomer components are used for the purpose of adjusting the physical properties (mechanical properties and adhesiveness to tooth substance in dental applications) of a cured product that forms the resin matrix. In this case, the type and amount of polymerizable monomers are preferably selected such that the polymerizable monomer component (a mixture of the monomers) have a refractive index of 1.38 to 1.55 so that the refractive index conditions mentioned above can be easily satisfied. Specifically, when a silica-titanium group element oxide-based composite oxide is used, which makes it easy to adjust the refractive index of the spherical inorganic particles, the resulting spherical inorganic particles will have a refractive index of about 1.45 to 1.58 depending on the silica content. Therefore, when the refractive index of the polymerizable monomer component is set in the range of 1.38 to 1.55, the refractive index of the resulting cured product can be adjusted in the range of about 1.40 to 1.57, which makes it easy to satisfy the conditions. The refractive indices of the polymerizable monomer component and the cured product of the polymerizable monomer component may be determined by measuring the refractive index for sodium D line (589 nm in wavelength) using an Abbe refractometer at 25° C. As used herein, the term "refractive index" means a refractive index for light with a wavelength of 589 nm at 25° C.

<Inorganic Particles (B)>

In the composite material of the present disclosure, the inorganic particles (B) dispersed in the resin matrix include one or more groups of identical diameter spherical particles (G-PID) and a group of superfine particles (G-SFP).

[Identical Diameter Spherical Particle Group (G-PID)]

The term "a group of identical diameter spherical particles (G-PID)" means a group of spherical inorganic particles having a specific average primary particle diameter in the range of 100 nm to 1,000 nm and having a number-size distribution in which 90% or more of all particles have particle diameters falling within the range of the average primary particle diameter−5% of the average primary particle diameter to the average primary particle diameter+5% of the average primary particle diameter. The individual spherical inorganic particles in the group consist essentially of the same material.

As used herein, the term "the average primary particle diameter of spherical inorganic particles" means the average of the primary particle diameters (maximum diameters) of 30 or more particles, which are observed and selected in a unit field of view of a G-PID photograph taken with a scanning electron microscope. The term "spherical" may mean "substantially spherical" and does not always have to mean "completely spherical". The particles in G-PID may have an average uniformity of 0.6 or more, preferably 0.8 or more, in which the average uniformity is determined by taking a photograph of G-PID with a scanning electron microscope, measuring the maximum diameter of each of (30 or more) particles in a unit field of view of the photograph, dividing, by the maximum diameter, the diameter of the particle in the direction perpendicular to the maximum diameter, and averaging the resulting quotients.

In the composite material of the present disclosure, the component particles in G-PID, which is a group of spherical inorganic particles with a narrow particle size distribution (number-size distribution), are dispersed in the resin matrix so as to have a specific short-range order structure, which allows light to undergo diffraction and interference according to the Bragg condition, so that light with a specific wavelength is strengthened to produce colored light with a color depending on the average primary particle diameter (to produce a structural color). Thus, in order to produce a structural color, 90% or more (by number) of the spherical inorganic particles in G-PID need to have primary particle diameters falling within the range of the average primary particle diameter−5% of the average primary particle diameter to the average primary particle diameter+5% of the average primary particle diameter. Moreover, in order to produce a structural color with a hue in a wide range from blue to yellow to red, the spherical inorganic particles in G-PID need to have an average primary particle diameter in the range of 100 nm to 1,000 nm. If spherical particles with an average primary particle diameter of less than 100 nm are used, interference of visible light and thus a structural color may be difficult to produce. If spherical particles with an average primary particle diameter of more than 1,000 nm are used, the spherical particles may settle out during the production of the composite material of the present disclosure or may reduce the grindability, which is not preferred, although the production of light interference can be expected.

When the average primary particle diameter is 230 nm to 800 nm, a structural color (colored light) of yellow to red is easy to produce. When the average primary particle diameter is 150 nm or more and less than 230 nm, a structural color (colored light) of blue is easy to produce.

In order to produce a structural color (colored light) of yellow to red, which is preferred for restoration treatment of natural teeth, G-PID preferably has an average primary particle diameter of 230 nm to 800 nm, more preferably 240 nm to 500 nm, even more preferably 260 nm to 350 nm. When G-PID with an average primary particle diameter in the range of 230 nm to 260 nm is used, the resulting colored light has a color of yellow, which is useful for the restoration of teeth in the category B (reddish yellow) according to the shade guide (VITA Classical available from VITA). When G-PID with an average primary particle diameter in the range of 260 nm to 350 nm is used, the resulting colored light has a color of red, which is useful for the restoration of teeth in the category A (reddish brown) according to the shade guide (VITA Classical available from VITA). The dentin often has a color with a hue of red. Therefore, use of only G-PID with an average primary particle diameter of 260 nm to 350 nm can provide a wide range of color conformity for restoration of teeth with various shades and thus is most preferred. When only G-PID with an average primary particle diameter in the range of 150 nm or more and less than 230 nm is used, the resulting colored light has a color of blue, which may be often unconformable with the color of the tooth substance with a cavity ranging from enamel to dentin but is useful for the restoration of enamel, in particular, useful for the restoration of incisal regions.

In the composite material of the present disclosure, the inorganic particles dispersed in the resin matrix may include one type of G-PID or multiple types of G-PID. The number A of the groups represented by G-PID is preferably 1 to 5, more preferably 1 to 3, even more preferably 1 or 2. When the inorganic particles include multiple types of G-PID, the material of the inorganic particles may be the same or different between the multiple types of G-PID.

In this regard, when the inorganic particles include multiple types of G-PID, one of the multiple types of G-PID needs to have an average primary particle diameter differing by 25 nm or more from that of any other of the multiple types of G-PID. In other words, when the inorganic particles include A types (e.g., A=3) of G-PID, each G-PID may be represented by G-PID$_m$, wherein m is 1 where A is 1 or m is a positive integer of 1 to A where A is 2 or more and the average primary particle diameter of G-PID increases with increasing m, and one G-PID$_m$ needs to have an average primary particle diameter $d_m$ differing by 25 nm or more from that of any other G-PID$_m$. For example, when A=3, $|d_1-d_2| \geq 25$ nm and $|d_2-d_3| \geq 25$ nm need to be satisfied (automatically, $|d_2-d_3| \geq 25$ nm is satisfied). When this condition is satisfied, for example, each G-PID can produce a unique structural color (according to each average primary particle diameter). This may be because each G-PID can contain such dispersed forms as dispersed aggregates each including a few (20 or less) spherical inorganic particles that are gathered with a very weak binding force so that each G-PID can have a short-range order structure capable of producing a structural color. In contrast, if this condition is not satisfied, the structural color will be difficult to produce. This may be because the whole of the spherical inorganic particles may have a broad particle size distribution, so that spherical inorganic particles may be dispersed and replaced between the multiple types of G-PID to cause a phenomenon similar to that in the case where a single group of inorganic particles not satisfying the number-size distribution condition is used.

When the composite material of the present disclosure includes multiple G-PID, the average primary particle diameters $d_m$ of each G-PID$_m$ preferably differ from each other by 30 nm or more, and more preferably differ from each other by 40 nm or more. In other words, the difference between $d_m$ and $d_{m-1}$ is preferably 30 nm or more, more preferably 40 nm or more. The difference between $d_m$ and $d_{m-1}$ is preferably 100 nm or less, more preferably 60 nm or less.

It should be noted that, when the composite material of the present disclosure contains multiple types of G-PID each having a very sharp size distribution and an average primary particle diameter difference as mentioned above, the size distributions of the multiple types of G-PID will hardly overlap each other, or even if partially overlapping each other, the size distributions of the multiple types of G-PID can be each identified. In other words, the inorganic particles in the composite material of the present disclosure will have the same number of size distribution peaks as the number of G-PID types in the composite material within the range of 100 nm to 1,000 nm, and even if the peaks partially overlap each other, the average primary particle diameter and number-size distribution of each G-PID can be identified using waveform processing. The particle size distribution of the inorganic particles may also be identified, for example, through image processing of an electron micrograph of an interior surface of the composite material of the present disclosure.

(Spherical Inorganic Particles)

The inorganic particles in G-PID may be made of any material as long as the G-PID conditions described above are satisfied. Preferred examples of the material for the inorganic particles include amorphous silica, silica-titanium group element oxide-based composite oxides (e.g., silica-zirconia, silica-titania), quartz, alumina, barium glass, strontium glass, lanthanum glass, fluoroaluminosilicate glass, ytterbium fluoride, zirconia, titania, and colloidal silica. Among them, silica-titanium group element oxide-based composite oxide particles are preferably used for ease of refractive index adjustment.

As used herein, the term "silica-titanium group element oxide-based composite oxide" means a composite oxide of silica and a titanium group element (Group 4 element of the Periodic Table) oxide. The refractive index of the silica-titanium group element oxide-based composite oxide may vary in the range of about 1.45 to about 1.58 depending on the silica content. Specific examples of the silica-titanium group element oxide-based composite oxide particles include silica-titania particles, silica-zirconia particles, and silica-titania-zirconia particles. Among them, silica-zirconia particles are preferred since they can provide high radiopacity. While silica and zirconia in the composite oxide may be in any ratio, the composite oxide preferably has a silica content of 70% by mole to 95% by mole and a titanium group element oxide content of 5% by mole to 30% by mole in order to provide sufficient radiopacity and a refractive index in the preferred range shown below.

The silica-titanium group element oxide-based composite oxide particles may contain a small amount of metal oxide other than silica and titanium group element oxide. Specifically, the silica-titanium group element oxide-based composite oxide particles may contain at most 10% by mole of alkali metal oxides, such as sodium oxide and lithium oxide.

The silica-titanium group element oxide-based composite oxide particles may be produced by any method. For example, a spherical filler of silica-titanium group element oxide-based composite oxide may be produced using what is called a sol-gel method, which includes adding, to an alkaline medium, a mixture solution containing a hydrolyzable organosilicon compound and a hydrolyzable organotitanium group metal compound; and subjecting the mixture to hydrolysis to precipitate the reaction product.

The spherical inorganic particles of the silica-titanium group element oxide-based composite oxide may be surface-treated with a silane coupling agent. When an organic-inorganic composite filler is produced as described below, the surface treatment with a silane coupling agent can increase the interface strength with the organic resin matrix of the organic-inorganic composite filler. Typical silane coupling agents include organosilicon compounds, such as γ-methacryloyloxyalkyltrimethoxysilane and hexamethyldisilazane. In the surface treatment, the silane coupling agent may be used in any amount. The optimal amount of the silane coupling agent may be determined through a preliminary experiment for checking the mechanical properties of the cured product of the polymerizable curable composition. For example, the silane coupling agent is preferably used in an amount of 0.1 parts by mass to 15 parts by mass based on 100 parts by mass of the spherical inorganic particles.

(Relationship Between Refractive Index of Resin Matrix and Refractive Index of Spherical Inorganic Particles)

The composite material of the present disclosure needs to satisfy the relation: $n_{(MX)} < n_{(G\text{-}PIDm)}$, wherein $n_{(MX)}$ is the refractive index of the resin matrix, and $n_{(G\text{-}PIDm)}$ is the refractive index of the spherical inorganic particles of each $G\text{-}PID_m$, for every $n_{(G\text{-}PIDm)}$. If the relation is not satisfied, short-wavelength light will be easily scattered in the resin matrix, even when a structural color is produced, so that the produced structural color will be difficult to see. For the visibility and clearness of the produced structural color and for the color conformity of the dental mill blank, the difference $\Delta n$ between $n_{(G\text{-}PIDm)}$ and $n_{(MX)}$ ($=n_{(G\text{-}PIDm)} - n_{(MX)}$) is preferably 0.001 to 0.1, more preferably 0.002 to 0.1, even more preferably 0.005 to 0.05.

As described above, the refractive index ($n_{(MX)}$) of the cured product, which forms the resin matrix, can be set in the range of 1.40 to 1.57 when the refractive index of the polymerizable monomer component (which may be a mixture of polymerizable monomers) is set in the range of 1.38 to 1.55. As described above, the refractive index $n_{(G\text{-}PIDm)}$ can be changed in the range of about 1.45 to about 1.58 by changing the silica content of the silica-titanium group element oxide-based composite oxide. Therefore, $\Delta n$ can be easily set in the preferred range by taking advantage of the relationships described above.

[Superfine Particle Group (G-SFP)]

The superfine particle group (G-SFP) is a group of inorganic particles with an average primary particle diameter of less than 100 nm, which is added for the purpose of adjusting the viscosity of the polymerizable curable composition as a precursor of the composite material of the present disclosure or adjusting the contrast ratio of the dental mill blank of the present disclosure. In this regard, G-SFP needs to have an average particle diameter that is 25 nm or more smaller than the average primary particle diameter ($d_1$) of G-PID$_1$, which is the smallest among those of G-PID of inorganic particles. If this condition is not satisfied, the state of dispersion of the spherical inorganic particles may be adversely affected so that it will be difficult to produce a structural color. The inorganic particles in G-SFP may have any shape and may be spherical or indefinite in shape. In general, the average primary particle diameter of G-SFP may have a lower limit of 2 nm.

For less effect on structural color production, G-SFP preferably has an average primary particle diameter of 3 nm to 75 nm, more preferably 5 nm to 50 nm. For the same purpose, G-SFP preferably has an average primary particle diameter that is 30 nm or more, more preferably 40 nm or more, smaller than the average primary particle diameter ($d_1$) of G-PID$_1$.

The inorganic particles in G-SFP may be made of any material similar to that for the spherical inorganic particles described above. The inorganic particles for G-SFP may also be surface-treated with a silane coupling agent, similar to the spherical inorganic particles. The preferred modes of the inorganic particles for G-SFP are basically the same as those of the spherical inorganic particles, except for those of the average primary particle diameter and the shape.

<Relationship Between the Composite Material of the Present Disclosure and the Polymerizable Curable Composition of the Present Disclosure>

The composite material of the present disclosure is preferably produced by polymerizing and curing the polymerizable curable composition of the present disclosure as a raw material. The content of each component in the composite material of the present disclosure is almost uniquely determined according to the composition of the polymerizable curable composition of the present disclosure. Moreover, the state of dispersion of the spherical inorganic particles in the composite material of the present disclosure (the dispersion structure) is considered to substantially directly result from the state of dispersion of the spherical inorganic particles in the polymerizable curable composition of the present disclosure (the dispersion structure) immediately before the curing. In other words, during the curing, the state of dispersion of the spherical inorganic particles may be affected by polymerization, shrinkage, and so on, but is not affected to such an extent as to change whether Conditions 1 and 2 are satisfied.

<Polymerizable Curable Composition of the Present Disclosure>

The polymerizable curable composition of the present disclosure contains a polymerizable monomer component (A), specifically, a polymerizable monomer component (A) capable of forming a cured product with a refractive index of 1.40 to 1.57; inorganic particles (B) including a group or groups of identical diameter spherical inorganic particles (G-PID) and a group of superfine particles (G-SFP), in which the identical diameter spherical inorganic particles and the superfine particles are made of a material or materials with a refractive index larger than that of the cured product made from the polymerizable monomer component (A); and a polymerization initiator (C). The polymerizable curable composition of the present disclosure is polymerized and cured to form a cured product that produces a structural color with a specific hue not dependent on the incident angle of light, which corresponds to the composite material of the present disclosure.

<Polymerizable Monomer Component (A) and Inorganic Particles (B)>

The polymerizable monomer component (A) in the polymerizable curable composition of the present disclosure is the same as the polymerizable monomer component (A) described above as a raw material for the resin matrix of the composite material of the present disclosure. G-PID, the spherical inorganic particles constituting G-PID, G-SFP, and the inorganic particles constituting G-SFP are also the same as those described above as components of the composite material of the present disclosure.

As mentioned above, the spherical inorganic particles of G-PID have an average primary particle diameter in the range of 100 nm to 1,000 nm. For ease to form the short-range order structure in the composite material of the present disclosure, G-PID preferably includes aggregate particles including aggregates of spherical inorganic particles. For example, G-PID preferably has an average aggregate particle diameter in the range of 5 μm to 200 μm, more preferably 10 μm to 100 μm. In this regard, the average aggregate particle diameter of G-PID may be calculated by the method described in the EXAMPLES section below.

The total content of G-PID in the polymerizable curable composition is typically 10 parts by mass to 1,500 parts by mass based on 100 parts by mass of the polymerizable monomer component (A). The total content of G-PID in the polymerizable curable composition is preferably 50 parts by mass to 1,500 parts by mass, more preferably 100 parts by mass to 1,500 parts by mass, based on 100 parts by mass of the polymerizable monomer component (A), so that the resulting composite material will have a suitable level of transparency and effectively produce a structural color. The polymerizable curable composition may contain multiple types of G-PID. In such a case, the content of each G-PID may be appropriately selected such that the total content of G-PID will fall within the range mentioned above, taking into account the hue of the structural color produced by each G-PID and the desired color of the dental mill blank.

The content of G-SFP in the polymerizable curable composition may be appropriately selected taking into account the viscosity of the polymerizable curable composition of the present disclosure, the contrast ratio of the dental mill blank of the present disclosure, and other properties. The content of G-SFP in the polymerizable curable composition is typically 0.1 parts by mass to 50 parts by mass, preferably 0.2 parts by mass to 30 parts by mass, based on 100 parts by mass of the polymerizable monomer component (A).

<Polymerization Initiator (C)>

The polymerization initiator in the polymerizable curable composition of the present disclosure may be any material having the function of polymerizing and curing the polymerizable monomer component. Methods for polymerizing the polymerizable curable composition include a reaction using light energy, such as ultraviolet or visible light (hereinafter, referred to as "photopolymerization"), a chemical reaction between a peroxide and an accelerator, and a reaction using thermal energy (hereinafter referred to as "thermal polymerization"), any of which may be used. Photopolymerization and thermal polymerization are preferred since any appropriate timing at which energy such as light or heat is added from outside can be selected for polymerization and the operation is simple. Thermal polymerization is more preferred since it is less likely to cause uneven polymerization and allows uniform polymerization.

Examples of the photopolymerization initiator that may be used include benzoin alkyl ethers, such as benzoin methyl ether, benzoin ethyl ether, and benzoin isopropyl ether; benzyl ketals, such as benzyl dimethyl ketal and benzyl diethyl ketal; benzophenone compounds, such as benzophenone, 4,4'-dimethylbenzophenone, and 4-methacryloxybenzophenone; α-diketones, such as diacetyl, 2,3-pentadione benzyl, camphorquinone, 9,10-phenanthraquinone, and 9,10-anthraquinone; thioxanthone compounds, such as 2,4-diethoxythioxanthone, 2-chlorothioxanthone, and methylthioxanthone; and bisacylphosphine oxides, such as bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, and bis (2,4,6-trimethylbenzoyl)-phenylphosphine oxide.

A reducing agent is often added to the photopolymerization initiator. Examples of such a reducing agent include tertiary amines, such as 2-(dimethylamino)ethyl methacrylate, ethyl 4-dimethylaminobenzoate, and N-methyldiethanolamine; aldehydes, such as lauryl aldehyde, dimethylaminobenzaldehyde, and terephthalaldehyde; sulfur-containing compounds, such as 2-mercaptobenzoxazole, 1-decanethiol, thiosalicylic acid, and thiobenzoic acid.

In many cases, the photopolymerization initiator and the reducing agent are used together with a photoacid generator. Examples of such a photoacid generator include a diaryliodonium salt compound, a sulfonium salt compound, a sulfonic ester compound, a halomethyl-substituted-S-triazine derivative, and a pyridinium salt compound.

Examples of the thermal polymerization initiator include peroxides, such as benzoyl peroxide, p-chlorobenzoyl peroxide, tert-butylperoxy-2-ethyl hexanoate, tert-butylperoxydicarbonate, and diisopropyl peroxydicarbonate; azo compounds, such as azobisisobutyronitrile; boron compounds, such as tributylborane, tributylborane partial oxide, sodium tetraphenylborate, sodium tetrakis(p-fluorophenyl) borate, and tetraphenylboric acid triethanolamine salt; barbituric acids, such as 5-butylbarbituric acid and 1-benzyl-5-phenylbarbituric acid; and sulfinic acid salts, such as sodium benzenesulfinate and sodium p-toluenesulfinate.

These polymerization initiators may be used alone, or a mixture of two or more of these polymerization initiators may be used. Multiple initiators for different types of polymerization may also be used in combination.

The effective amount of the polymerization initiator may be selected depending on the purpose. The amount of the polymerization initiator is typically 0.01 parts by mass to 10 parts by mass, preferably 0.1 parts by mass to 5 parts by mass, based on 100 parts by mass of the polymerizable monomer component.

The polymerization using the thermal polymerization initiator is preferably carried out at a temperature of 60° C. to 200° C., more preferably 70° C. to 150° C., even more preferably 80° C. to 130° C. If the polymerization is performed at a temperature of less than 60° C., a dental mill blank with a low strength may be produced in which cracking may occur. If the polymerization is performed at a temperature of more than 200° C., the composite material of the present disclosure being produced may be exposed to high temperature so that the resin component may undergo discoloration, which may make it difficult to obtain color conformity with natural teeth.

<Preferred Modes of the Polymerizable Curable Composition of the Present Disclosure>

In the polymerizable curable composition of the present disclosure, at least some of the particles in one or more groups of identical diameter spherical particles are preferably in the form of an organic-inorganic composite filler containing one group of identical diameter spherical particles and a resin with a refractive index lower than that of the spherical inorganic particles of the one group and not containing any other group of identical diameter spherical particles than the one group (in other words, an organic-inorganic composite filler containing only a single type of G-PID).

As used herein, the term "organic-inorganic composite filler" means a filler made of a powder of a composite containing an (organic) resin matrix and an inorganic filler dispersed in the resin matrix or a coagulated material in which the primary particles of an inorganic filler are bonded together with an (organic) resin.

According to the preferred mode, for example, when the composition contains three types of G-PID with different average primary particle diameters, namely, $G\text{-}PID_1$, $G\text{-}PID_2$, and $G\text{-}PID_3$, all or some of the particles in at least one of the groups in the composition are in the form of an organic-inorganic composite filler containing only one G-PID. If all particles in $G\text{-}PID_1$ are in the form of an organic-inorganic composite filler containing only $G\text{-}PID_1$ (composite filler 1) in the polymerizable curable composition, the composite filler 1 contains only $G\text{-}PID_1$ and can provide a short-range order structure that produces a $G\text{-}PID_1$-specific structural color. In this case, therefore, the composite material of the present disclosure, which is a cured product of the polymerizable curable composition of the present disclosure, reliably produces a $G\text{-}PID_1$-specific structural color. If $G\text{-}PID_1$ is not in the form of a composite filler in the composition, it will be mixed with $G\text{-}PID_2$ and $G\text{-}PID_3$, which are added (not in the form of a composite) simultaneously with $G\text{-}PID_1$, so that a certain proportion of the particles in $G\text{-}PID_1$ and $G\text{-}PID_2$ will be replaced with each other, and nearest neighbor spherical inorganic particles in $G\text{-}PID_1$ will form $G\text{-}PID_3$, which may destroy the short-range order structure in a region around such spherical inorganic particles. On the other hand, if all particles of $G\text{-}PID_1$ are in the form of a composite filler 1, the mutual replacement of particles will not occur, and the short-range order structure will not be destroyed. Therefore, the content of spherical inorganic particles not involved in the production of a structural color can be reduced as much as possible, so that the composite material obtained after the curing will reliably produce a $G\text{-}PID_1$-specific structural color. $G\text{-}PID_2$ and/or $G\text{-}PID_3$ may also be in the form of an organic-inorganic composite filer (composite filler 2) containing only $G\text{-}PID_2$ and/or in the form of an organic-inorganic composite filler (composite filler 3) containing only $G\text{-}PID_3$ to make it possible to reliably produce structural colors specific for them.

Preferably, 10% to 90%, more preferably 20% to 80%, even more preferably 30% to 70% of the particles in each G-PID are in the form of an organic-inorganic composite filler containing only one G-PID, so that the advantageous effect mentioned above will be expected and the viscosity of the polymerizable curable composition of the present disclosure can be easily adjusted.

When G-PID is blended in a form other than "an organic-inorganic composite filler containing only one G-PID", it is generally blended in the form of a powder (G-PID itself as a group of spherical inorganic particles), but alternatively, spherical inorganic particles may be blended in the form of an organic-inorganic composite filler containing multiple types of G-PID. Hereinafter, the organic-inorganic composite filler will be described in detail, including this form.

(Organic-Inorganic Composite Filler)

As mentioned above, the term "organic-inorganic composite filler" means a filler made of a powder of a composite containing an (organic) resin matrix and an inorganic filler dispersed in the resin matrix or a coagulated material in which the primary particles of an inorganic filler are bonded together with an (organic) resin.

In the polymerizable curable composition of the present disclosure, the organic-inorganic composite filler includes spherical inorganic particles as an inorganic filler and a resin having a refractive index smaller than that of the spherical inorganic particles, which forms the (organic) resin matrix. The resin may be any type satisfying the conditions mentioned above. Preferably, the resin is a cured product of the polymerizable monomer component for use to form the resin matrix of the composite material of the present disclosure. While the resin does not have to include the same component as the polymerizable monomer component of the polymerizable curable composition of the present disclosure, the resin preferably includes a component with the same refractive index as that of the polymerizable monomer component. Every organic-inorganic composite filler needs to satisfy the relation $n_{(R)} < n_{(F)}$, wherein $n_{(R)}$ is the refractive index of the resin, and $n_{(F)}$ is the refractive index of the spherical inorganic particles. When the organic-inorganic composite filler contains different types of spherical inorganic particles with different refractive indices, the relation needs to be satisfied for each type of spherical inorganic particles. Δn between $n_{(F)}$ and $n_{(R)}$ ($=n_{(F)}-n_{(R)}$) is preferably 0.001 to 0.01, more preferably 0.001 to 0.005.

The content of the spherical inorganic particles in the organic-inorganic composite filler is preferably 30% by mass to 95% by mass. When the content of the spherical inorganic particles in the organic-inorganic composite filler is 30% by mass or more, the polymerizable curable composition of the present disclosure can form a cured product that has sufficiently high mechanical strength and produces desired colored light. It is operationally difficult to obtain an organic-inorganic filler uniformly containing more than 95% by mass of spherical inorganic particles. The content of the spherical inorganic particles in the organic-inorganic composite filler is more preferably 40% by mass to 90% by mass.

The organic-inorganic composite filler may be produced by a general production method that includes mixing specific amounts of spherical inorganic particles, a polymerizable monomer component, and a polymerization initiator; subjecting the mixture to polymerization by heating, light irradiation, or other methods; and then pulverizing the polymerization product. Such a production method yields an organic-inorganic composite filler having an indefinite shape and comprising a composite including a resin matrix and spherical inorganic particles dispersed in the resin matrix.

The organic-inorganic composite filler may also be produced by the method disclosed in WO 2011/115007 or WO 2013/039169, which specifically includes immersing aggregate particles including aggregates of spherical inorganic particles in a liquid composition containing a polymerizable monomer component, a polymerization initiator, and an organic solvent; then removing the organic solvent; and polymerizing and curing the polymerizable monomer component by heating, light irradiation, or other methods. Such a method makes it possible to obtain a porous organic-inorganic composite filler having a large number of fine pores communicating with the outside and including spherical inorganic primary particles, which substantially remain in the form of aggregates; and a resin that covers at least part of the surface of each of the primary particles and binds the primary particles together.

The average particle diameter of the organic-inorganic composite filler is preferably, but not limited to, 2 μm to 100 μm, more preferably 5 μm to 50 μm, even more preferably 5 μm to 30 μm, in order to provide a high mechanical strength for the composite material of the present disclosure or to provide good handleability for the polymerizable curable composition of the present disclosure.

A pigment, a polymerization inhibitor, a fluorescent whitening agent, and other materials (usually in an amount of 0.0001 parts by mass to 5 parts by mass based on 100 parts by mass of the organic-inorganic composite filler) may be added to the organic-inorganic composite filler as long as its effects are not impaired. The organic-inorganic composite filler may also be subjected to washing or surface treatment with a silane coupling agent or the like.

The content of the organic-inorganic composite filler in the polymerizable curable composition of the present disclosure may be calculated and determined from the content of the spherical inorganic particles in the organic-inorganic composite filler such that the total content of G-PID (namely, the total content of the spherical inorganic particles) falls within the range mentioned above, taking into account the content of the group of identical diameter spherical particles not in the form of the organic-inorganic composite filler in the polymerizable curable composition.

<Other Additives>

The polymerizable curable composition of the present disclosure may contain other additives, such as a polymerization inhibitor and an ultraviolet absorber, as long as its effects are not impaired.

As described above, the composite material of the present disclosure obtained from the polymerizable curable composition of the present disclosure produces a structural color even without any colorant such as a pigment. Therefore, there is no need to add a pigment, which may undergo discoloration over time, to the polymerizable curable composition of the present disclosure. However, the addition of a pigment is not prohibited, and the polymerizable curable composition may contain a pigment in such an amount that it will not interfere with colored light produced by interference by the spherical filler. Specifically, the polymerizable curable composition may contain a pigment in an amount of about 0.0005 parts by mass to about 0.5 parts by mass, preferably about 0.001 parts by mass to about 0.3 parts by mass, based on 100 parts by mass of the polymerizable monomer component.

<Methods of Producing the Composite Material of the Present Disclosure and the Dental Mill Blank of the Present Disclosure>

Next, a method of producing the composite material of the present disclosure and a method of producing the dental mill blank of the present disclosure will be described.

A method of producing the composite material of the present disclosure also corresponds to one step in a method of producing the dental mill blank of the present disclosure. Specifically, a method of producing the dental mill blank of the present disclosure having a milling target portion in a specific shape includes mixing a polymerizable monomer component (A), inorganic particles (B), and a polymerization initiator (C) to form a polymerizable curable composition, wherein the polymerizable monomer component (A) is capable of forming a cured product having a refractive index of 1.40 to 1.57, the inorganic particles (B) included a group or groups of identical diameter spherical particles including a material having a refractive index higher than that of the cured product made from the polymerizable monomer component (A) and a group of superfine particles; and subjecting the polymerizable curable composition to cast molding and polymerization to form a composite material bulk body that forms the whole or part of the milling target portion, wherein the mixing is carried out so as to form a polymerizable curable composition capable of forming a cured product containing spherical inorganic particles that form all of a group or groups of identical diameter spherical particles and have a short-range order structure satisfying the Conditions 1 and 2 as an arrangement structure.

The polymerizable curable composition prepared in the mixing step has a composition substantially the same as that of the polymerizable curable composition of the present disclosure described above. Kneading and degassing allow the inorganic particles (B) to be dispersed in the polymerizable monomer component (A) such that the composition can form a cured product containing spherical inorganic particles having, as an arrangement structure, a short-range order structure satisfying Conditions 1 and 2 shown above.

The kneading method is preferably performed using a kneader, such as a planetary centrifugal mixer, which can satisfy the necessary dispersion conditions in a short period of time and easily achieve scale-up production. The degassing preferably includes degassing under reduced pressure, which can remove air bubbles in a short period of time from a composition with high viscosity.

In the method, the kneading and the degassing should be performed under kneading and degassing conditions that have been confirmed as to whether the polymerizable curable composition (the polymerizable curable composition of the present disclosure) to be prepared in the step can form a cured product in which the inorganic particles (B) are dispersed in a state satisfying Conditions 1 and 2 shown above.

The method for determining the kneading and degassing conditions is preferably the method (1) or (2) shown below.

(1) A method that includes preliminarily performing mixing under different sets of kneading and degassing conditions to form a polymerizable curable composition having a composition the same or substantially the same as that of the polymerizable curable composition to be produced actually; examining the radial distribution function $g(r)$ with respect to a cured product of the polymerizable curable composition prepared under each set of conditions to determine conditions for satisfying Conditions 1 and 2 shown above; and taking conditions the same as the determined conditions.

(2) A method that includes sampling a portion of the composition obtained during kneading and degassing and/or after the completion of kneading and degassing; checking whether the inorganic particles (B) dispersed in a curing reaction product of the sampled composition is in a state satisfying Conditions 1 and 2 shown above; and continuing the kneading and/or the degassing until the conditions are satisfied.

When the method (1) is employed, for example, the kneading and degassing conditions may be determined as shown below. First, plural types of simulated kneading processes each including using a planetary centrifugal mixer (planetary mixer), which is a device for the actual process, to mix raw materials for a polymerizable curable composition having a composition the same as that of the polymerizable curable composition to be produced actually are performed under different conditions, such as different speeds of ration, different kneading periods of time, and different degassing conditions after the kneading. Next, the radial distribution function $g(r)$ with respect to a cured product of the polymerizable curable composition obtained in each of the simulated kneading processes is examined in order to determine the cured product satisfying Conditions 1 and 2 shown above. The method (1) makes it possible to reliably produce a desired polymerizable curable composition only through setting specific kneading conditions. Therefore, the method (1) can eliminate the need to change the conditions each time for the production of the same polymerizable curable composition (the same in composition and amount) and prevent excessive kneading (kneading for an unnecessarily long period of time) and thus can improve the efficiency of the operation.

The method (2) is considered a particularly preferred method for producing a polymerizable curable composition different in composition or amount each time.

The polymerizable curable composition of the present disclosure is subjected to cast molding and polymerization to form a composite material bulk body that forms the whole or part of the milling target portion. As used herein, the term "cast molding and polymerization" means a process that includes charging the polymerizable curable composition of the present disclosure into a mold in a specific shape; and then polymerizing and curing the composition. The mold may have any volume appropriately selected depending on the desired shape. The mold may have any shape, such as a prismatic shape, a cylindrical shape, a rectangular plate shape, a disk shape, or any other irregular shape. During the polymerization, if necessary, pressurization with an inert gas, such as nitrogen, may be performed. A mold having a shape the same or substantially the same as that of the milling target portion may be provided, into which the polymerizable curable composition of the present disclosure may be charged and then polymerized and cured to form a bulk body, which may be used directly as the milling target portion. Alternatively, a mold having a size larger than the size of the milling target portion may be provided, into which the composition may be charged and then polymerized and cured to form a bulk body, which may be subjected to punching or milling to form the milling target portion. The charging of the composition into the mold may be performed using any known method, such as injection, extrusion, or pressing. In the charging process, a single polymerizable curable composition may be charged, or multiple polymerizable curable compositions different in composition may be charged to form a multilayer material. The polymerizable curable composition of the present disclosure may also be charged together with another polymerizable curable composition as any other raw resin material to form a multilayer material.

The mold may be made of metal, ceramic, or resin depending on the purpose, and is preferably made of a heat-resistant material that is resistant to the temperature at which the polymerization is performed. Examples of the material of the mold include stainless steel (SUS), high-speed tool steel, aluminum alloys, polyethylene terephthalate (PET), polyethylene (PE), polypropylene (PP), and polystyrene (PS).

If necessary, the resulting bulk body may also be subjected to subsequent steps, such as heat treatment, polishing, milling, attachment of fasteners, and printing. If necessary, a fastening pin for fixing the dental mill blank to a milling machine may be joined to the bulk body. The fastening pin may have any shape that allows the dental mill blank to be fixed to a milling machine. The fastening pin may also be omitted depending on the shape of the dental mill blank and the requirements from the processing machine. The fastening pin may be made of, for example, stainless steel, brass, or aluminum. Methods for fixing the fastening pin to the milling target portion (the main body of the dental mill blank) include not only adhesive bonding but also fitting and screw fixation. The adhesive bonding may be performed by any method using any commercially available adhesive, such as an isocyanate, epoxy, urethane, silicone, or acrylic adhesive.

EXAMPLES

Hereinafter, the present invention will be more specifically described with reference to examples, which are not intended to limit the present invention.

Dental mill blanks of examples and comparative examples were each obtained through curing a polymerizable curable composition containing a polymerizable monomer component, inorganic particles, and a polymerization initiator. First, each component used to form the polymerizable curable composition of each of the examples and the comparative examples will be described.

1. Polymerizable Monomer Component

The mixtures M1 and M2 shown in Table 1, which are each a mixture of polymerizable monomers, were each used as the polymerizable monomer component. The abbreviations in the polymerizable monomer column of the table represent the following compounds, and each value in the parentheses represents the content in units of parts by mass.

UDMA: 1,6-bis(methacrylethyloxycarbonylamino)trimethylhexane
3G: Triethylene glycol dimethacrylate
bis-GMA: 2,2-bis[(3-methacryloyloxy-2-hydroxypropyloxy)phenyl]propane The viscosities of M1 and M2 were measured in a constant temperature room at 25° C. using an E-type viscometer (VISCONIC ELD manufactured by Tokyo Keiki Inc.).

The refractive index before curing (M1 or M2) and the refractive index after curing (cured product) were measured in a constant temperature room at 25° C. using an Abbe refractometer (manufactured by Atago Co., Ltd.). The cured product sample was prepared by a process including adding, to 100 parts by mass of M1 or M2, 0.2% by mass of camphorquinone (CQ), 0.3% by mass of ethyl p-N,N-dimethylaminobenzoate (DMBE), and 0.15% by mass of hydroquinone monomethyl ether (HQME) as photopolymerization initiators; mixing them uniformly; adding the mixture to a mold having a through hole of 7 mmφ×0.5 mm; then bringing polyester films into press contact with both sides of the mixture; then curing the mixture by light irradiation for 30 seconds using a dental halogen light irradiator (Demetron LC manufactured by Sybron) with a light dose of 500 mW/cm$^2$; and then taking the cured product out of the mold. When the cured product sample was placed in the Abbe refractometer, a drop of a medium (bromonaphthalene), in which the sample was not soluble and which had a refractive index higher than that of the sample, was placed on the sample in order to bring the sample in close contact with the measurement surface.

TABLE 1

| Polymerizable monomer | Polymerizable monomer viscosity [mPa · s] | Refractive index Before curing | Refractive index After curing |
|---|---|---|---|
| M1 UDMA(60)/3G(40) | 150.14 | 1.474 | 1.509 |
| M2 bis-GMA(60)/3G(40) | 755.65 | 1.515 | 1.546 |

2. Inorganic Particles 2-1. Group of Identical Diameter Spherical Particles (G-PID)

G-PID1 to G-PID11 shown in Table 2 were used as G-PID. These groups of identical diameter spherical particles were prepared according to the method disclosed in Japanese Unexamined Patent Application, Publication No. S58-110414 or S58-156524 (what is called sol-gel method). Specifically, first, a mixture solution containing a hydrolyzable organosilicon compound (e.g., tetraethyl silicate) and a hydrolyzable organotitanium group metal compound (e.g., tetrabutyl zirconate, tetrabutyl titanate) in a such a ratio as to provide the composition shown in the composition column of Table 2 was added to an ammonia-containing solution of an alcohol (e.g., methanol, ethanol, isopropyl alcohol, isobutyl alcohol) and then subjected to hydrolysis to give a reaction product precipitate. Subsequently, the precipitate was separated, then dried, optionally pulverized, and then fired to give a fired material. Subsequently, 100 parts by mass of the fired material was mixed and stirred with 4 parts by mass of γ-methacryloyloxypropyltrimethoxysilane and 3 parts by mass of n-propylamine in 500 parts by mass of methylene chloride. After the methylene chloride was removed using an evaporator, the resulting product was dried by heating at 90° C. to give a group of surface-treated, identical diameter, spherical particles.

The average primary particle diameter, the average aggregate particle diameter, the content of average diameter particles, the average uniformity, and the refractive index shown in Table 2 were measured as shown below.

(1) Average Primary Particle Diameter

A photograph of the powder was taken with a scanning electron microscope (XL-30S manufactured by Philips) at a magnification of 5,000 to 100,000 and then subjected to image processing using image analysis software (IP-1000PC manufactured by Asahi Kasei Engineering Corporation), in which the number (at least 30) and primary particle diameters (maximum particle diameters) of particles observed in a unit field of view of the photograph were determined. The number average primary particle diameter was calculated from the determined values using the formula below.

$$\bar{x} = \frac{\sum_{i=1}^{n} x_i}{n} \text{(Number average)}$$

($n$: number of particles, $x_i$: primary particle diameter (maximum diameter) of $i$-th particle)

(2) Average Aggregate Particle Diameter

A dispersion of 0.1 g of G-PID in 10 mL of ethanol was prepared and thoroughly shaken by hand. The volume cumulative median diameter of the particles in the dispersion was determined using a laser diffraction-scattering particle size distribution analyzer (LS230 manufactured by Beckman Coulter) and the optical model Fraunhofer. The resulting median diameter was used as the average aggregate particle diameter of G-PID.

(3) Content of Average Diameter Particles (the Proportion (%) of Particles with Sizes Falling within the Range of Average Primary Particle Diameter±5% of Average Primary Particle Diameter in Number-Size Distribution to all Particles)

The number of particles having primary particle diameters (maximum sizes) out of the range of the average primary particle diameter−5% of the average primary particle diameter to the average primary particle diameter+5% of the average primary particle diameter, which was determined as shown above, was counted among all particles in the unit field of view of the photograph. The number of particles with primary particle diameters falling within the range of the average primary particle diameter−5% of the average primary particle diameter to the average primary particle diameter+5% of the average primary particle diameter was calculated by subtracting the count from the number of all particles. The content of average diameter particles was calculated from the formula below.

The content (%) of average diameter particles=[(the number of particles with primary particle diameters falling within the range of the average primary particle diameter±5% of the average primary particle diameter in the unit field of view of the scanning electron micrograph)/(the number of all particles in the unit field of view of the scanning electron micrograph)]×100

(4) Average Uniformity

A photograph of the powder was taken with a scanning electron microscope. The number (n: at least 30) of particles in a group of identical diameter spherical particles (G-PID) observed in a unit field of view of the photograph was counted, and the long diameter (Li) (maximum size) and short diameter (Bi) (the size in a direction perpendicular to the long diameter) of each of the particles were determined. The average uniformity of the particles was calculated from the formula below.

$$\text{Average uniformity} = \frac{\sum_{i=1}^{n} Bi/Li}{n}$$

(5) Refractive Index

The refractive index was measured by an immersion method using an Abbe refractometer (manufactured by Atago Co., Ltd.). Specifically, a group of identical diameter spherical particles (G-PID) were dispersed in 50 mL of anhydrous toluene in a 100 mL sample bottle in a constant temperature room at 25° C. While the resulting dispersion was stirred with a stirrer, 1-bromotoluene was slowly added dropwise to the dispersion, during which the refractive index of the dispersion was determined when the dispersion reached the clearest state. The resulting value was used as the refractive index of the group of identical diameter spherical particles (G-PID).

(manufactured by Sakamoto Giken) having a rotary disk for centrifugal spray. The rotation speed of the disk was 10,000 rpm, and the temperature of the drying atmospheric air was 200° C. The powder obtained by the spray dry granulation was then vacuum dried at 60° C. for 18 hours to give 73 g of substantially spherical aggregates.

Subsequently, 50 g of the aggregates were immersed in a polymerizable monomer solution composed of a mixture of 10 g of the polymerizable monomer component M1, 0.025 g of azobisisobutyronitrile (AIBN) as a thermal polymerization initiator, and 5.0 g of methanol as an organic solvent (containing 36 parts by mass of the polymerizable monomer component based on 100 parts by mass of the organic solvent). The mixture resulting from thorough stirring was checked for whether it was in the form of a slurry, and then allowed to stand for 1 hour.

The resulting mixture was transferred to a rotary evaporator. While being stirred, the mixture was dried at a reduced pressure of 10 hPa under heating conditions at 40° C. (using a warm water bath) for 1 hour so that the organic solvent was removed. A powder with high fluidity was obtained as a result of the removal of the organic solvent. While being stirred in a rotary evaporator, the resulting powder was heated at a reduced pressure of 10 hPa under conditions at 100° C. (using an oil bath) for 1 hour so that the polymerizable monomer component in the powder was polymerized and cured. As a result of this process, 45 g of a substantially spherical, organic-inorganic composite filler (CF1) was obtained, including spherical aggregates and an organic polymer covering the surface of the aggregates. The organic-inorganic composite filler had an average particle size of 33 μm.

TABLE 2

| | Composition and shape of filler | | Average primary particle diameter (nm) | Average aggregate particle diameter (μm) | Refractive index | Content of average diameter particles (%) | Average uniformity |
|---|---|---|---|---|---|---|---|
| | Composition (mol %) SiO$_2$/ZrO$_2$/Na$_2$O | Shape | | | | | |
| G-PID1 | 89.8/9.0/1.2 | Spherical | 80 | 24.2 | 1.515 | 91 | 0.98 |
| G-PID2 | 89.8/9.0/1.2 | Spherical | 200 | 61.7 | 1.515 | 93 | 0.97 |
| G-PID3 | 89.8/9.0/1.2 | Spherical | 238 | 44.5 | 1.515 | 96 | 0.95 |
| G-PID4 | 89.8/9.0/1.2 | Spherical | 250 | 30.2 | 1.515 | 95 | 0.92 |
| G-PID5 | 89.8/9.0/1.2 | Spherical | 262 | 27.6 | 1.515 | 95 | 0.94 |
| G-PID6 | 89.8/9.0/1.2 | Spherical | 275 | 50.8 | 1.515 | 92 | 0.93 |
| G-PID7 | 89.8/9.0/1.2 | Spherical | 280 | 32.8 | 1.515 | 94 | 0.93 |
| G-PID8 | 89.8/9.0/1.2 | Spherical | 295 | 107.3 | 1.515 | 92 | 0.94 |
| G-PID9 | 89.8/9.0/1.2 | Spherical | 331 | 55.2 | 1.515 | 92 | 0.92 |
| G-PID10 | 89.8/9.0/1.2 | Spherical | 367 | 33.5 | 1.515 | 90 | 0.94 |
| G-PID11 | 89.8/9.0/1.2 | Spherical | 400 | 12.7 | 1.515 | 91 | 0.94 |
| F1 | 89.8/9.0/1.2 | Indefinite shape | 500 | — | 1.515 | 50 | — |

2-2. Organic-Inorganic Composite Filler (CF1)

To 200 g of water was added 100 g of the group of identical diameter spherical particles (G-PID5) shown in Table 2. The particles were dispersed using a circulation type pulverizer SC Mill (manufactured by Nippon Coke & Engineering Co., Ltd.) to form an aqueous dispersion.

Separately, 4 g (0.016 mol) of γ-methacryloyloxypropyltrimethoxysilane and 0.003 g of acetic acid were added to 80 g of water and stirred for 1 hour and 30 minutes to form a uniform solution of pH 4. The solution was added to the aqueous dispersion, and they were mixed to uniformity. Subsequently, the dispersion being lightly mixed was supplied to onto a disk being rotated at high speed so that the dispersion was subjected to granulation by spray drying. The spray drying was performed using a spray dryer TSR-2W 2-3. Superfine Particles (G-SFP)

The G-SFP used was Reolosil QS-102 (12 nm in average primary particle diameter, manufactured by Tokuyama Corporation).

2-4. Indefinite Shaped Inorganic Particles

Indefinite shaped inorganic particles F1 shown in Table 2 were used. Indefinite shaped inorganic particles F1 were prepared according to the method disclosed in, for example, Japanese Unexamined Patent Application, Publication No. H02-132102 or H03-197311, which included dissolving an alkoxysilane compound in an organic solvent; adding water to the solution to cause partial hydrolysis; then further adding an alkoxide of another metal and an alkali metal compound, which were for forming a composite material, to the partial hydrolysis product; allowing the hydrolysis to proceed to form a gel material; then drying the gel material; optionally pulverizing the dried material; and firing the dried material. As shown above for G-PID, the indefinite shaped inorganic particles were measured for average primary particle diameter (which means the average particle diameter of the pulverized indefinite shaped inorganic particles), average diameter particle content, and refractive index.

3. Polymerization Initiator

The polymerization initiator used was a photopolymerization initiator composed of a combination of camphorquinone (CQ) and ethyl p-N,N-dimethylaminobenzoate (DMBE) or a thermal polymerization initiator composed of benzoyl peroxide (BPO).

Example 1

To 100 parts by mass of the polymerizable monomer component M1 was added 0.3 parts by mass of CQ and 1.0 part by mass of DMBE and mixed to form a uniform polymerizable monomer composition. Subsequently, 500 parts by mass of G-PID4 and 1.0 part by mass of the superfine particle group (G-SFP) were weighed, to which the polymerizable monomer composition was gradually added under red light, while the mixture was thoroughly kneaded using a planetary mixer (manufactured by Inoue Mfg. Inc.) to form a uniform curable paste. The paste was degassed under reduced pressure so that air bubbles were removed, thereby giving a polymerizable curable composition. The resulting polymerizable curable composition was charged into a prismatic mold (14 mm×18 mm×150 mm) made of polypropylene while air bubbles were prevented from being trapped into the composition. Subsequently, after the upper surface of the composition was smoothed, the composition was irradiated for 1 minute with light from a dental LED polymerizer (a Light V manufactured by Morita Corporation). The resulting cured product was taken out of the mold to give a dental mill blank.

Figure 1B:
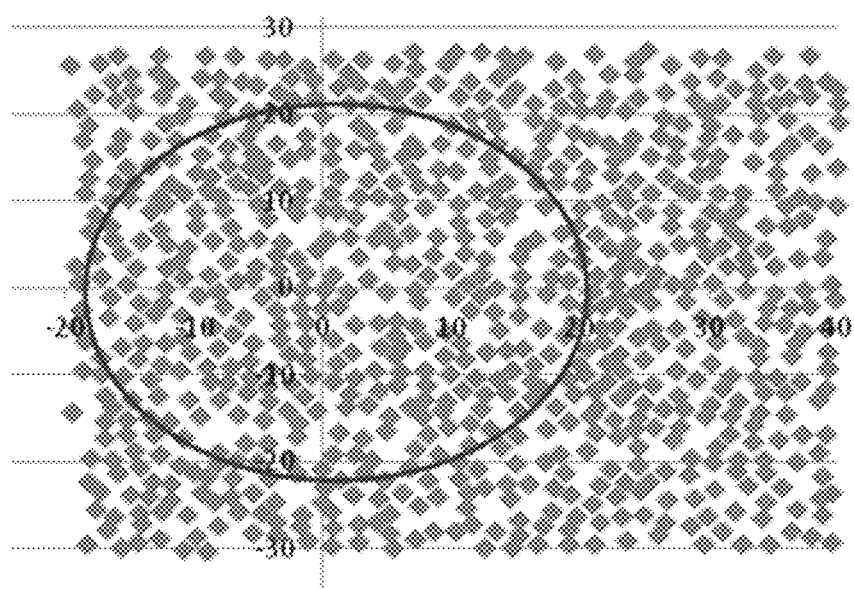
FIG. 1B is a view showing an example of coordinate data obtained from the scanning electron microscopy image of FIG. 1A.
Figure 2:
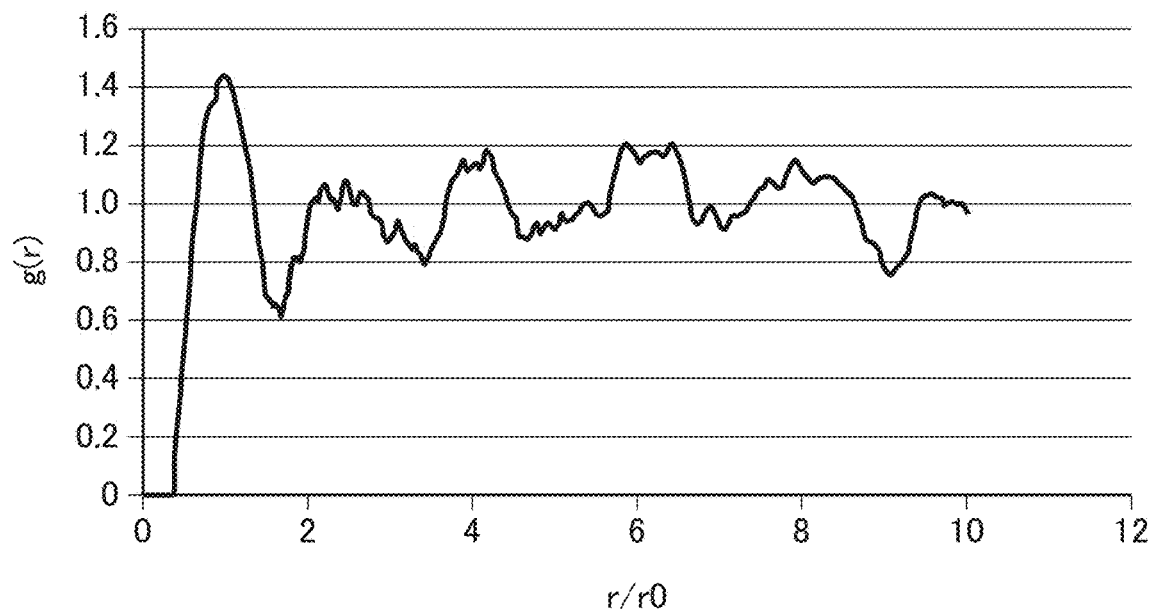
FIG. 2 is a graph showing a radial distribution function g(r) calculated based on the parameters determined from the coordinate data in FIG. 1B.

The resulting dental mill blank was subjected to (1) visual evaluation of colored light, (2) measurement of colored light wavelength, (3) evaluation of color conformity using a colorimeter, (4) visual evaluation of color conformity, (5) evaluation of the radial distribution function of spherical inorganic particles, (6) visual evaluation of appearance, and (7) evaluation of bending strength. Tables 3 to 5 show the composition of each dental mill blank (note: the matrix column shows the polymerizable monomer component used to form the resin matrix) and the evaluation results. FIG. 1A shows an example of an image of a plane of a piece of a cured product cut from the dental mill blank of Example 1, which was observed with a scanning electron microscope. FIG. 1B shows an example of coordinate data obtained from the scanning electron microscopy image of FIG. 1A. FIG. 2 is a graph showing a radial distribution function g(r) calculated based on the parameters determined from the coordinate data in FIG. 1B. In Example 1, a dental mill blank was successfully obtained, satisfying Conditions 1 and 2 with respect to radial distribution function, which were reproduced 10 times out of 10 times, and being evaluated to have a uniform appearance with no cracks. Each evaluation and measurement were performed using the method shown below.

(1) Visual Evaluation of Colored Light

A piece of the cured product with a length of at least 7 mm and a thickness of 1 mm was cut from the dental mill blank of each of the examples and the comparative examples and used as an evaluation sample. The resulting evaluation sample was vertically mounted on the adhesive surface of an about 10 mm square black tape (carbon tape), and the color of colored light from the sample was visually observed.

(2) Wavelength of the Colored Light

An evaluation sample was prepared as in the section (1). The spectral reflectivity of the sample was measured on each of a black background and a white background using a color difference meter (TC-1800 MKII manufactured by Tokyo Denshoku Co., Ltd.). The wavelength at the local maximum point of the reflectivity measured on the black background was determined to be the wavelength of the colored light.

(3) Evaluation of Color Conformity Using Colorimeter

Simulated restoration was performed on hard resin teeth with a class II cavity (5 mm in diameter, 3 mm in depth) reproduced at the lower right sixth tooth. The dental mill blank of each of the examples and the comparative examples was subjected to milling to form a dental prosthesis (restoration) conformable to the missing portion. The dental prosthesis was bonded to the cavity with EsteCem II (adhesive resin cement manufactured by Tokuyama Dental Corporation) and then polished so that the restoration was completed. The color conformity of the simulated restoration portion was evaluated using a two-dimensional colorimeter (RC-500 manufactured by PaPaLab Co., Ltd.). The hard resin teeth used were high-chroma hard resin teeth (corresponding to A4) and low-chroma hard resin teeth (corresponding to A1) falling within the category A (reddish brown) according to the shade guide (VITA Classical available from VITA); and high-chroma hard resin teeth (corresponding to B4) and low-chroma hard resin teeth (corresponding to B1) falling within the category B (reddish yellow) according to the shade guide (VITA Classical available from VITA).

The hard resin teeth were placed in the two-dimensional colorimeter and imaged. The resulting image was analyzed using image analysis software (RC Series Image Viewer manufactured by PaPaLab Co., Ltd.). The color difference ($\Delta E^*$ for CIELab) between the measured color values of the restored portion and the non-restored portion in the hard resin teeth was determined and evaluated for color conformity.

$$\Delta E^* = \{(\Delta L^*)^2 + (\Delta a^*)^2 + (\Delta b^*)^2\}^{1/2}$$

$$\Delta L^* = L1^* - L2^*$$

$$\Delta a^* = a1^* - a2^*$$

$$\Delta b^* = b1^* - b2^*$$

In the formula, $L1^*$ is the lightness index of the restored portion in the hard resin teeth, $a1^*$ and $b1^*$ are the color index of the restored portion in the hard resin teeth, $L2^*$ is the lightness index of the non-restored portion in the hard resin teeth, $a2^*$ and $b2^*$ are the color index of the non-restored portion in the hard resin teeth, and $\Delta E^*$ is the amount of change in color.

(4) Visual Evaluation of Color Conformity

As shown in the section (3), simulated restoration was performed, and the color conformity of the restored portion was visually evaluated. The evaluation criteria are as follows.

—Evaluation Criteria—

5: The color of the restoration is indistinguishable from that of the hard resin teeth.

4: The color of the restoration conforms well with that of the hard resin teeth.

3: The color of the restoration resembles that of the hard resin teeth.
2: The color of the restoration resembles but does not conform well with that of the hard resin teeth.
1: The color of the restoration does not conform with that of the hard resin teeth.

(5) Evaluation of the Radial Distribution Function of Spherical Inorganic Particles A 5 mmφ×10 mm piece of the cured product was cut from the dental mill blank of each of the examples and the comparative examples. The state of dispersion of spherical particles in the piece of the cured product was observed with a scanning electron microscope (XL-30S manufactured by Philips), when the radial distribution function of the particles was determined and evaluated. Specifically, the piece of the cured product was subjected to cross-sectional milling under conditions at 2 kV for 20 minutes using an ion milling system (IM4000 manufactured by Hitachi, Ltd.) so that a plane to be observed (observation plane) was formed. A region of the observation plane, containing 1,000 spherical particles, was imaged with a scanning electron microscope. The resulting scanning electron microscopy image was analyzed using image analysis software (Simple Digitizer ver. 3.2 (free software)), and the coordinates of the spherical particles in the region were determined. The coordinates of any one of the spherical particles were selected from the resulting coordinate data. A circle with a radius r was drawn with its center at the selected spherical particle, in which r is the distance covering an area containing at least 200 spherical particles from the center. The number of the spherical particles in the circle was counted and used to calculate the average particle density <ρ> (in units of counts per cm$^2$). The number dn of the particles in the region between the circle with its circumference apart by the distance r from the spherical particle at the center and a circle with its circumference apart by a distance of r+dr from the spherical particle at the center was counted, and the area da of the region was calculated, in which dr was a value in the range of about $r_0/100$ to about $r_0/10$, in which $r_0$ was the average particle diameter of the spherical particles. The resulting values <ρ>, dn, and da were used to calculate the radial distribution function g(r) according to Formula (1) below.

$$g(r) = \{1 / <\rho>\} \times \{dn / da\} \quad (1)$$

A graph is plotted showing the relationship between the radial distribution function and $r/r_0$, in which r is any distance from the center of the circle, and $r_0$ is the average particle diameter of the spherical particles. The resulting radial distribution function was rated "S" when satisfying Conditions 1 and 2, and rated "N" when not satisfying any of Conditions 1 and 2.

(6) Visual Evaluation of Appearance

The appearance of the dental mill blank of each of the examples and the comparative examples was visually observed and rated "S" when not having any crack or other defects, and rated "N" when having a crack.

(7) Evaluation of Bending Strength

Test pieces with a width of 2 mm and a length of 25 mm were cut from the dental mill blank of each of the examples and the comparative examples. The test pieces were polished in its longitudinal direction with water-resistant polishing paper #1500 to give test pieces with a thickness of 2 mm±0.1 mm. The resulting test pieces were subjected to a three-point bending test using a universal tensile testing machine (Autograph manufactured by Shimadzu Corporation) under the conditions of a span of 20 mm and a crosshead speed of 1 mm/minute in the room temperature atmosphere. The bending strengths of five of the test pieces were measured and used to calculate the average bending strength.

TABLE 3

| | Resin matrix | Identical diameter spherical particle group | Superfine particle group | Refractive index difference* | Visual evaluation of colored light | Colored light wavelength (nm) on black background | Colored light wavelength (nm) on white background | Radial distribution function Condition 1 | Radial distribution function Condition 2 | Appearance evaluation | Bending strength (Mpa) |
|---|---|---|---|---|---|---|---|---|---|---|---|
| Example 1 | M1(100) | G-PID4(500) | G-SFP(1) | 0.006 | Yellow | 607 | No maximum | S | S | S | 175 |
| Example 2 | M1(100) | G-PID5(200)/G-PID8(200) | G-SFP(1) | 0.006 | Red | 695 | No maximum | S | S | S | 180 |
| Example 3 | M1(100) | G-PID4(200)/G-PID7(100)/G-PID9(100)/G-PID10(100)/G-PID11(100) | G-SFP(1) | 0.006 | Red | 756 | No maximum | S | S | S | 190 |
| Example 4 | M1(100) | CF1(300)/G-PID5(200) | G-SFP(1) | 0.006 | Red | 720 | No maximum | S | S | S | 195 |
| Example 5 | M1(100) | G-PID4(500) | G-SFP(1) | 0.006 | Yellow | 607 | No maximum | S | S | S | 200 |
| Example 6 | M1(100) | CF1(300)/G-PID5(200) | G-SFP(1) | 0.006 | Red | 720 | No maximum | S | S | S | 205 |
| Comparative Example 1 | M2(100) | G-PID4(400) | G-SFP(1) | −0.031 | Blue | 481 | No maximum | — | — | S | 181 |
| Comparative Example 2 | M1(100) | G-PID2(400) | G-SFP(1) | 0.006 | Deep Blue | 430 | No maximum | S | N | N | — |
| Comparative Example 3 | M1(100) | G-PID1(400) | G-SFP(1) | 0.006 | None | 405 | No maximum | — | — | S | 173 |

TABLE 3-continued

| | Resin matrix | Identical diameter spherical particle group | Superfine particle group | Refractive index difference* | Visual evaluation of colored light | Colored light wavelength (nm) on black background | Colored light wavelength (nm) on white background | Radial distribution function Condition 1 | Radial distribution function Condition 2 | Appearance evaluation | Bending strength (Mpa) |
|---|---|---|---|---|---|---|---|---|---|---|---|
| Comparative Example 4 | M1(100) | F1(400) | G-SFP (1) | 0.006 | None | No maximum | No maximum | — | — | S | 150 |
| Comparative Example 5 | M1(100) | G-PID3(100)/ G-PID4(200)/ G-PID5(200)/ G-PID6(100) | G-SFP (1) | 0.006 | None | No maximum | No maximum | — | — | S | 190 |

*(Refractive index of identical diameter spherical particle group (G-PID)) − (refractive index of polymer in resin matrix)

TABLE 4

| | Category A (reddish brown) color conformity | | | |
|---|---|---|---|---|
| | Low chroma | | High chroma | |
| | Visual evaluation | ΔE* | Visual evaluation | ΔE* |
| Example 1 | 4 | 0.82 | 4 | 0.85 |
| Example 2 | 5 | 0.18 | 5 | 0.25 |
| Example 3 | 5 | 0.20 | 4 | 0.85 |
| Example 4 | 5 | 0.29 | 5 | 0.28 |
| Example 5 | 4 | 0.91 | 4 | 0.87 |
| Example 6 | 5 | 0.31 | 5 | 0.30 |
| Comparative Example 1 | 2 | 3.67 | 2 | 3.89 |
| Comparative Example 2 | 1 | 8.53 | 1 | 8.37 |
| Comparative Example 3 | 1 | 4.87 | 1 | 4.93 |
| Comparative Example 4 | 2 | 3.99 | 1 | 4.71 |
| Comparative Example 5 | 2 | 3.98 | 2 | 3.89 |

TABLE 5

| | Category B (reddish yellow) color conformity | | | |
|---|---|---|---|---|
| | Low chroma | | High chroma | |
| | Visual evaluation | ΔE* | Visual evaluation | ΔE* |
| Example 1 | 5 | 0.32 | 5 | 0.20 |
| Example 2 | 5 | 0.34 | 4 | 0.95 |
| Example 3 | 5 | 0.33 | 4 | 0.88 |
| Example 4 | 5 | 0.31 | 5 | 0.35 |
| Example 5 | 5 | 0.41 | 5 | 0.33 |
| Example 6 | 5 | 0.35 | 5 | 0.42 |
| Comparative Example 1 | 1 | 4.66 | 1 | 4.85 |
| Comparative Example 2 | 1 | 7.86 | 1 | 7.94 |
| Comparative Example 3 | 1 | 4.88 | 1 | 4.91 |
| Comparative Example 4 | 2 | 3.98 | 1 | 4.81 |
| Comparative Example 5 | 2 | 3.92 | 2 | 3.79 |

Example 2

Figure 3:
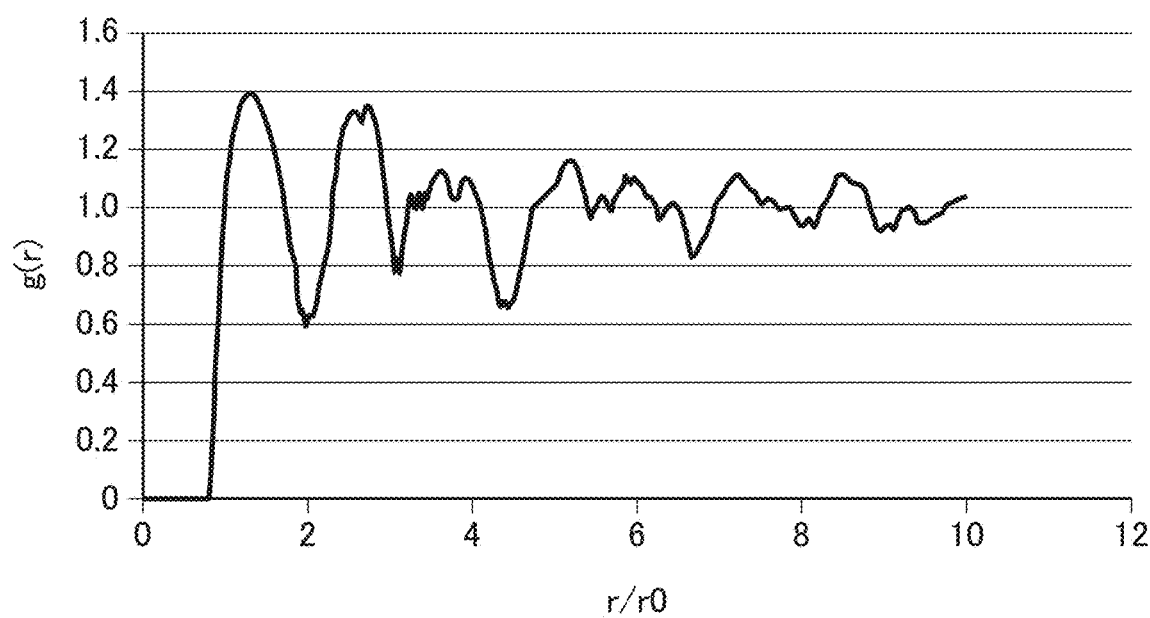
FIG. 3 is a graph showing a radial distribution function with respect to a piece of a cured product cut from the dental mill blank of Example 2.

A dental mill blank was obtained as in Example 1 except that the composition of the dental mill blank was changed as shown in Table 3. As in Example 1, the resulting dental mill blank was subjected to (1) visual evaluation of colored light, (2) measurement of colored light wavelength, (3) evaluation of color conformity using a colorimeter, (4) visual evaluation of color conformity, (5) evaluation of the radial distribution function of spherical inorganic particles, (6) visual evaluation of appearance, and (7) evaluation of bending strength. Tables 3 to 5 show the evaluation results. FIG. 3 shows the radial distribution function graph with respect to the piece of the cured product cut from the dental mill blank of Example 2. In Example 2, a dental mill blank was also successfully obtained, satisfying Conditions 1 and 2 with respect to radial distribution function, which were reproduced 10 times out of 10 times, and being evaluated to have a uniform appearance with no cracks.

Example 3

To 200 parts by mass of the polymerizable monomer component M1 was added 0.6 parts by mass of CQ and 2.0 parts by mass of DMBE and mixed to form a uniform polymerizable monomer composition. Subsequently, 200 parts by mass of G-PID4, 200 parts by mass of G-PID7, 200 parts by mass of G-PID10, and 1.0 part by mass of the superfine particle group (G-SFP) were weighed and mixed with 100 parts by mass of the polymerizable monomer composition under red light. The mixture was thoroughly kneaded using a planetary mixer (manufactured by Inoue Mfg. Inc.) to form a uniform curable paste 1. Separately, 200 parts by mass of G-PID4, 200 parts by mass of G-PID9, 200 parts by mass of G-PID11, and 1.0 part by mass of the superfine particle group (G-SFP) were weighed and mixed with 100 parts by mass of the polymerizable monomer composition under red light. The mixture was thoroughly kneaded using a planetary mixer (manufactured by Inoue Mfg. Inc.) to form a uniform curable paste 2. The resulting curable pastes 1 and 2 were each degassed under reduced pressure so that air bubbles were removed, thereby giving polymerizable curable compositions 1 and 2. Each of the resulting polymerizable curable compositions 1 and 2 was charged into a prismatic mold (14 mm×18 mm×10 mm) made of polypropylene while air bubbles were prevented from being trapped into the composition. Subsequently, after the upper surface of each composition was smoothed, the curable compositions 1 and 2 in the molds were placed on each other (14 mm×18 mm×20 mm) with their smoothed surfaces in close contact with each other, and then irradiated for 1 minute with light from a dental LED polymerizer (a Light V manufactured by Morita Corporation). The resulting cured product was taken out of the molds to give a dental mill blank.

Figure 4:
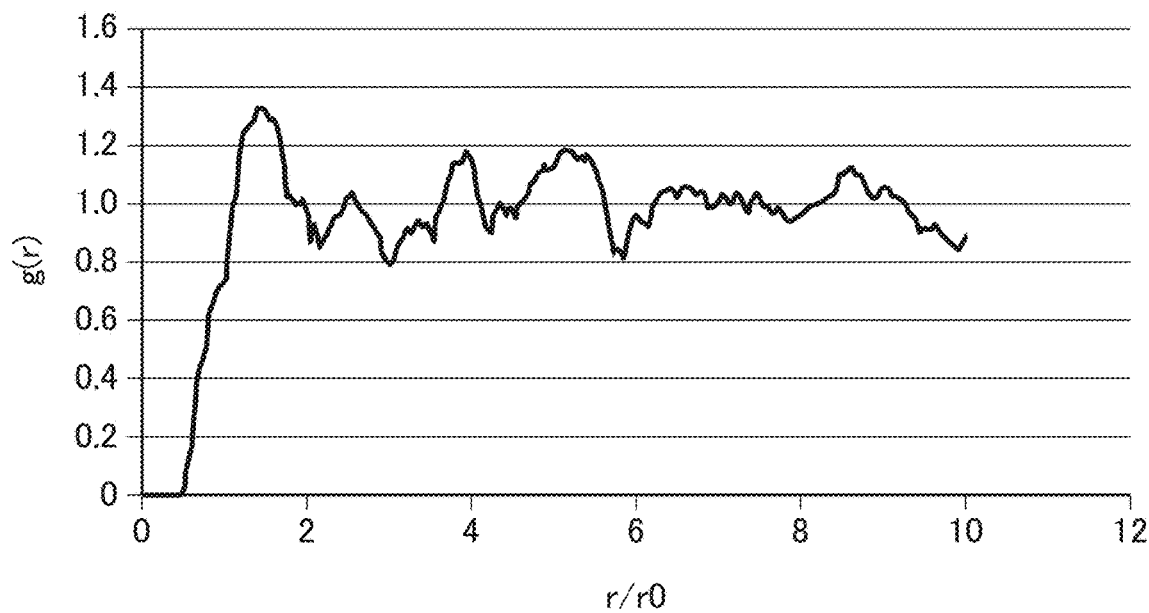
FIG. 4 is a graph showing a radial distribution function with respect to a piece of a cured product cut from the dental mill blank of Example 3.

As in Example 1, the resulting dental mill blank was subjected to (1) visual evaluation of colored light, (2) measurement of colored light wavelength, (3) evaluation of color conformity using a colorimeter, (4) visual evaluation of color conformity, (5) evaluation of the radial distribution function of spherical inorganic particles, (6) visual evaluation of appearance, and (7) evaluation of bending strength. Tables 3 to 5 show the evaluation results. FIG. 4 shows the radial distribution function graph with respect to the piece of the cured product cut from the dental mill blank of Example 3. In Example 3, a dental mill blank was also successfully obtained, satisfying Conditions 1 and 2 with respect to radial distribution function, which were reproduced 10 times out of 10 times, and being evaluated to have a uniform appearance with no cracks.

Example 4

Figure 5:
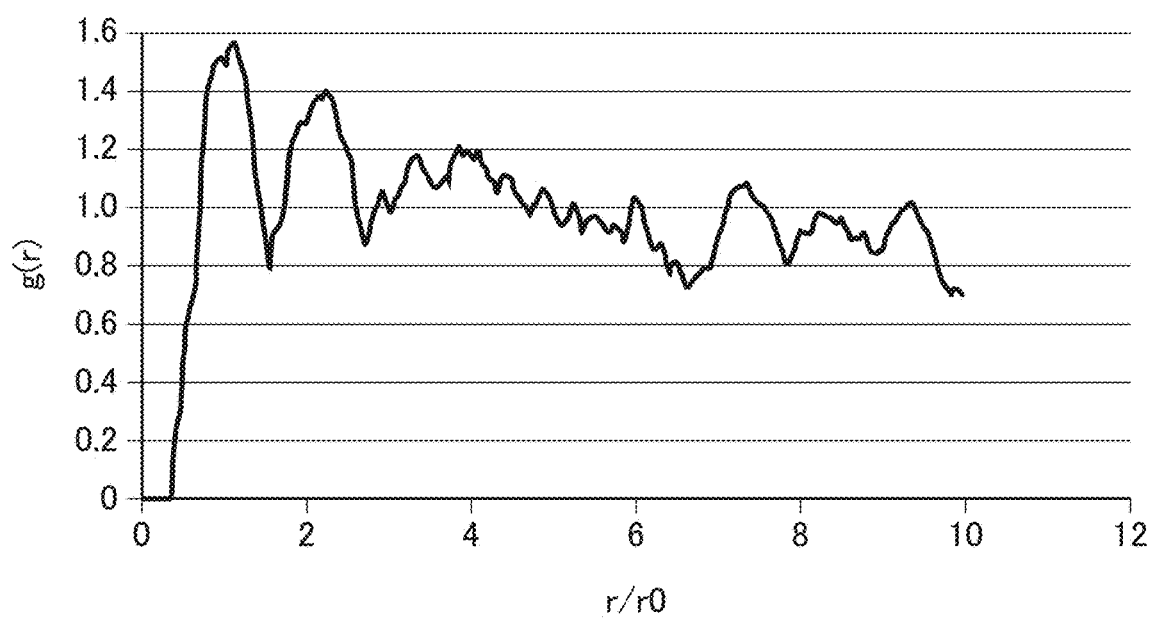
FIG. 5 is a graph showing a radial distribution function with respect to a piece of a cured product cut from the dental mill blank of Example 4.

A dental mill blank was obtained as in Example 1 except that the composition of the dental mill blank was changed as shown in Table 3. As in Example 1, the resulting dental mill blank was subjected to (1) visual evaluation of colored light, (2) measurement of colored light wavelength, (3) evaluation of color conformity using a colorimeter, (4) visual evaluation of color conformity, (5) evaluation of the radial distribution function of spherical inorganic particles, (6) visual evaluation of appearance, and (7) evaluation of bending strength. Tables 3 to 5 show the evaluation results. FIG. 5 shows the radial distribution function graph with respect to the piece of the cured product cut from the dental mill blank of Example 4. In Example 4, a dental mill blank was also successfully obtained, satisfying Conditions 1 and 2 with respect to radial distribution function, which were reproduced 10 times out of 10 times, and being evaluated to have a uniform appearance with no cracks.

Example 5

To 100 parts by mass of the polymerizable monomer component M1 was added 0.5 parts by mass of BPO and mixed to form a uniform polymerizable monomer composition. Subsequently, 500 parts by mass of G-PID4 and 1.0 part by mass of the superfine particle group (G-SFP) were weighed, to which the polymerizable monomer composition was gradually added under red light, while the mixture was thoroughly kneaded using a planetary mixer (manufactured by Inoue Mfg. Inc.) to form a uniform curable paste. The paste was degassed under reduced pressure so that air bubbles were removed, thereby giving a polymerizable curable composition. The resulting polymerizable curable composition was charged into a prismatic mold (14 mm×18 mm×150 mm) made of polypropylene while air bubbles were prevented from being trapped into the composition. Subsequently, after the upper surface of the composition was smoothed, the composition was subjected to pressure heating polymerization using a heat pressure polymerizer under pressurized conditions at a nitrogen pressure of 0.4 MPa and 100° C. for 12 hours. The resulting cured product was taken out of the mold to give a dental mill blank.

Figure 6:
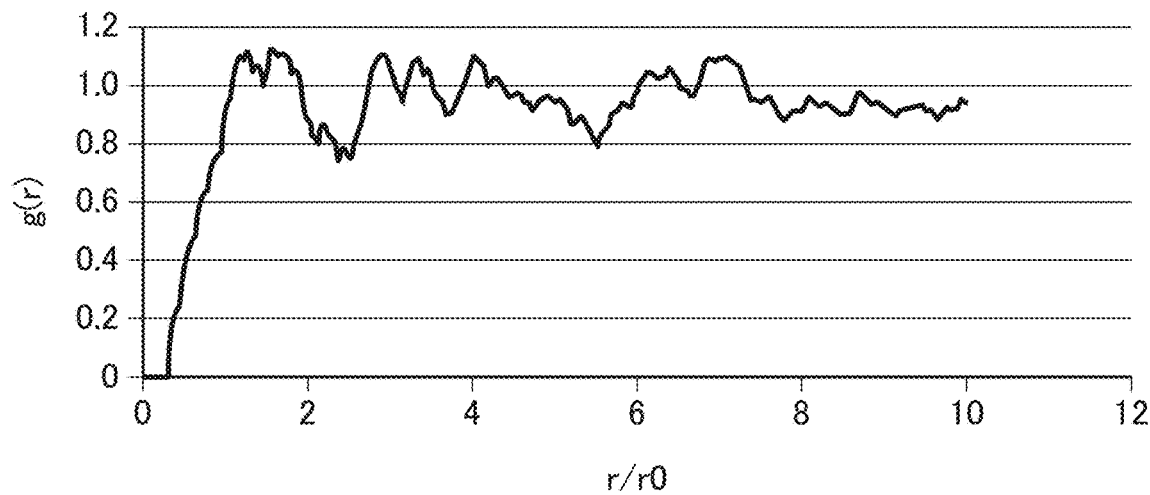
FIG. 6 is a graph showing a radial distribution function with respect to a piece of a cured product cut from the dental mill blank of Example 5.

As in Example 1, the resulting dental mill blank was subjected to (1) visual evaluation of colored light, (2) measurement of colored light wavelength, (3) evaluation of color conformity using a colorimeter, (4) visual evaluation of color conformity, (5) evaluation of the radial distribution function of spherical inorganic particles, (6) visual evaluation of appearance, and (7) evaluation of bending strength. Tables 3 to 5 show the evaluation results. FIG. 6 shows the radial distribution function graph with respect to the piece of the cured product cut from the dental mill blank of Example 5. In Example 5, a dental mill blank was also successfully obtained, satisfying Conditions 1 and 2 with respect to radial distribution function, which were reproduced 10 times out of 10 times, and being evaluated to have a uniform appearance with no cracks.

Example 6

Figure 7:
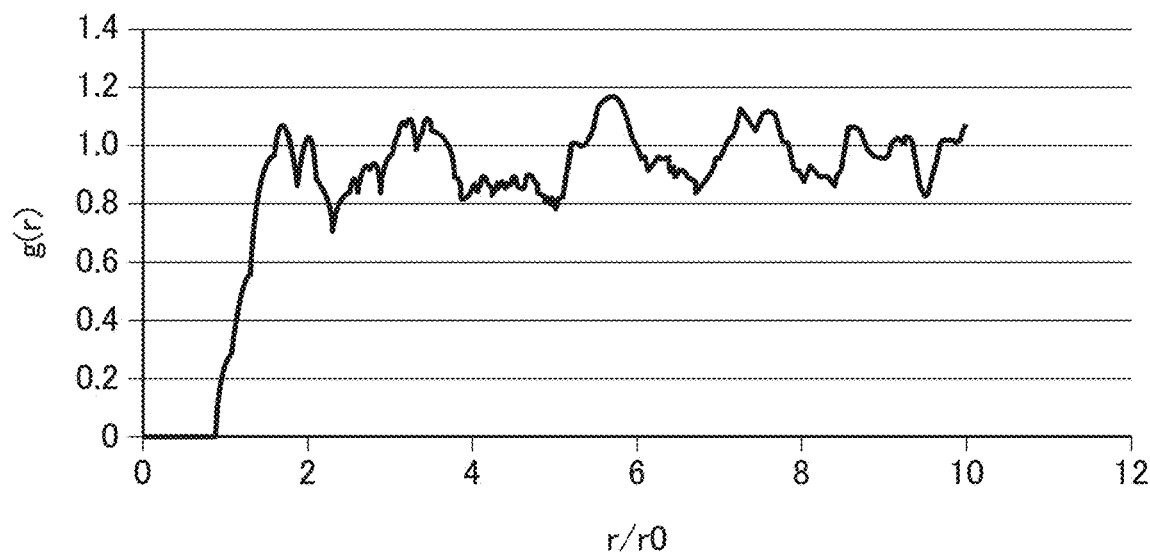
FIG. 7 is a graph showing a radial distribution function with respect to a piece of a cured product cut from the dental mill blank of Example 6.

A dental mill blank was obtained as in Example 5 except that the composition of the dental mill blank was changed as shown in Table 3. As in Example 1, the resulting dental mill blank was subjected to (1) visual evaluation of colored light, (2) measurement of colored light wavelength, (3) evaluation of color conformity using a colorimeter, (4) visual evaluation of color conformity, (5) evaluation of the radial distribution function of spherical inorganic particles, (6) visual evaluation of appearance, and (7) evaluation of bending strength. Tables 3 to 5 show the evaluation results. FIG. 7 shows the radial distribution function graph with respect to the piece of the cured product cut from the dental mill blank of Example 6. In Example 6, a dental mill blank was also successfully obtained, satisfying Conditions 1 and 2 with respect to radial distribution function, which were reproduced 10 times out of 10 times, and being evaluated to have a uniform appearance with no cracks.

Comparative Examples 1 and 3 to 5

A dental mill blank was obtained as in Example 1 except that the composition of the dental mill blank was changed as shown in Table 3. As in Example 1, the resulting dental mill blank was subjected to (1) visual evaluation of colored light, (2) measurement of colored light wavelength, (3) evaluation of color conformity using a colorimeter, (4) visual evaluation of color conformity, (6) visual evaluation of appearance, and (7) evaluation of bending strength. Tables 3 to 5 show the evaluation results.

Comparative Example 2

To 100 parts by mass of the polymerizable monomer component M1 was added 0.3 parts by mass of CQ and 1.0 part by mass of DMBE and mixed to form a uniform polymerizable monomer composition. Subsequently, 400 parts by mass of G-PID2 and 1.0 part by mass of the superfine particle group (G-SFP) were weighed, to which the polymerizable monomer composition was gradually added under red light, while the mixture was kneaded in a mortar to form a curable paste. The paste was degassed under reduced pressure so that air bubbles were removed, thereby giving a polymerizable curable composition. The resulting polymerizable curable composition was charged into a prismatic mold (14 mm×18 mm×150 mm) made of polypropylene while air bubbles were prevented from being trapped into the composition. Subsequently, after the upper surface of the composition was smoothed, the composition was irradiated for 1 minute with light from a dental LED polymerizer (a Light V manufactured by Morita Corporation). The resulting cured product was taken out of the mold to give a dental mill blank.

As in Example 1, the resulting dental mill blank was subjected to (1) visual evaluation of colored light, (2) measurement of colored light wavelength, (3) evaluation of color conformity using a colorimeter, (4) visual evaluation of color conformity, (5) evaluation of the radial distribution function of spherical inorganic particles, and (6) visual evaluation of appearance. Tables 3 to 5 show the evaluation results. In Comparative Example 2, the evaluation was not good at a rate of 1 out of 5. Such evaluation results are shown in the table. In Comparative Example 2, the bending strength was not able to be evaluated because cracking was observed in the visual appearance evaluation test.

The results of Examples 1 to 6 demonstrate that the cured products satisfying the conditions according to the present invention show colored light on a black background and have good color conformity.

The results shown in FIGS. 1A, 1B, and 2 demonstrate that the dental mill blank obtained in Example 1 has a short-range order structure according to the present invention because the radial distribution function g(r) has the first maximum peak observed at a position where the distance $r_1$ between nearest neighbor particles is 1.03 times the particle size $r_0$ ($r_1/r_0$ is 1.03) and because the radial distribution function g(r) has a local minimum value of 0.60 between the distance $r_1$ between nearest neighbor particles and the distance $r_2$ between second nearest neighbor particles.

The results shown in FIG. 3 demonstrate that the dental mill blank obtained in Example 2 has a short-range order structure according to the present invention because the radial distribution function g(r) has the first maximum peak observed at a position where the distance $r_1$ between nearest neighbor particles is 1.24 times the particle size $r_0$ ($r_1/r_0$ is 1.24) and because the radial distribution function g(r) has a local minimum value of 0.62 between the distance $r_1$ between nearest neighbor particles and the distance $r_2$ between second nearest neighbor particles.

The results shown in FIG. 4 demonstrate that the dental mill blank obtained in Example 3 has a short-range order structure according to the present invention because the radial distribution function g(r) has the first maximum peak observed at a position where the distance $r_1$ between nearest neighbor particles is 1.41 times the particle size $r_0$ ($r_1/r_0$ is 1.41) and because the radial distribution function g(r) has a local minimum value of 0.88 between the distance $r_1$ between nearest neighbor particles and the distance $r_2$ between second nearest neighbor particles.

The results shown in FIG. 5 demonstrate that the dental mill blank obtained in Example 4 has a short-range order structure according to the present invention because the radial distribution function g(r) has the first maximum peak observed at a position where the distance $r_1$ between nearest neighbor particles is 1.04 times the particle size $r_0$ ($r_1/r_0$ is 1.04) and because the radial distribution function g(r) has a local minimum value of 0.80 between the distance $r_1$ between nearest neighbor particles and the distance $r_2$ between second nearest neighbor particles.

The results shown in FIG. 6 demonstrate that the dental mill blank obtained in Example 5 has a short-range order structure according to the present invention because the radial distribution function g(r) has the first maximum peak observed at a position where the distance $r_1$ between nearest neighbor particles is 1.24 times the particle size $r_0$ ($r_1/r_0$ is 1.24) and because the radial distribution function g(r) has a local minimum value of 1.00 between the distance $r_1$ between nearest neighbor particles and the distance $r_2$ between second nearest neighbor particles.

The results shown in FIG. 7 demonstrate that the dental mill blank obtained in Example 6 has a short-range order structure according to the present invention because the radial distribution function g(r) has the first maximum peak observed at a position where the distance $r_1$ between nearest neighbor particles is 1.68 times the particle size $r_0$ ($r_1/r_0$ is 1.68) and because the radial distribution function g(r) has a local minimum value of 0.86 between the distance $r_1$ between nearest neighbor particles and the distance $r_2$ between second nearest neighbor particles.

The results of Comparative Examples 1 and 3 to 5 demonstrate that the cured products not satisfying any of the conditions according to the present invention do not have a desired color ($n_{(Mx)} < n_{(G-PIDm)}$ is not satisfied in Comparative Example 1), do not show colored light on a black background (G-PID has an average particle diameter of 80 nm in Comparative Example 3; the filler has an indefinite shape in Comparative Example 4; the difference between the average primary particle diameters of the particles of the individual groups represented by G-PID$_m$ is less than 25 nm in Comparative Example 5), and have low color conformity.

The results of Comparative Example 2 demonstrate that the composition resulting from non-uniform kneading does not satisfy the conditions for the arrangement structure of spherical inorganic particles according to the present invention and provides low color conformity with the tooth substance.

The results shown in FIG. 8 demonstrate that the dental mill blank obtained in Comparative Example 2 does not has a short-range order structure according to the present invention because the radial distribution function g(r) has the first maximum peak observed at a position where the distance $r_1$ between nearest neighbor particles is 1.58 times the particle size $r_0$ ($r_1/r_0$ is 1.58) and because the radial distribution function g(r) has a local minimum value of 0.18 between the distance $r_1$ between nearest neighbor particles and the distance $r_2$ between second nearest neighbor particles.

The invention claimed is:

1. A dental mill blank, comprising a milling target portion comprising a resin-based material,
    the resin-based material comprising at least one composite material comprising a resin matrix and inorganic particles dispersed in the resin matrix,
    the inorganic particles comprising:
    at least one group of identical diameter spherical particles (G-PID) comprising spherical inorganic particles with a specific average primary particle diameter in a range of 100 nm to 1,000 nm and having a number-size distribution in which 90% or more of all particles have particle diameters falling within a range of the average primary particle diameter-5% of the average primary particle diameter to the average primary particle diameter+5% of the average primary particle diameter; and
    a group of superfine particles (G-SFP) comprising inorganic particles with an average primary particle diameter of less than 100 nm,
    the at least one group including one or more groups of identical diameter spherical particles, wherein
    the one or more groups of identical diameter spherical particles are A groups each represented by G-PID$_m$, wherein A is the number of the groups, m is 1 where A is 1 or m is a positive integer of 1 to A where A is 2 or more, and the average primary particle diameter of the group increases with increasing m,
    the groups represented by G-PID$_m$ have average primary particle diameters differing by 25 nm or more from each other,
    the group of superfine particles has an average primary particle diameter 25 nm or more smaller than that of the group represented by G-PID$_1$,
    the at least one composite material satisfies the relation $n_{(Mx)} < n_{(G-PIDm)}$, wherein $n_{(Mx)}$ is a refractive index of the resin matrix for light with a wavelength of 589 nm at 25° C., $n_{(G\text{-}PIDm)}$ is a refractive index of the spherical inorganic particles of each group represented by $G\text{-}PID_m$ for light with a wavelength of 589 nm at 25° C., and the relation is satisfied for each $n_{(G\text{-}PIDm)}$, and the at least one composite material has a short-range order structure in which the spherical inorganic particles of all the groups of identical diameter spherical particles in the resin matrix have an arrangement structure satisfying:

Condition 1 where a radial distribution function graph plotted with $r/r_0$ on an x axis and a radial distribution function g(r) on a y axis and showing a relationship between $r/r_0$ and the g(r) for r, wherein $r/r_0$ is a normalized dimensionless number calculated by dividing a distance r from a center of any spherical inorganic particle in the composite material by an average particle diameter $r_0$ of all spherical inorganic particles dispersed in the composite material and the g(r) represents a probability of existence of any other spherical inorganic particle at a point apart by the distance r from the center of the any spherical inorganic particle, has peaks among which a peak closest to an origin provides a distance $r_1$ between nearest neighbor particles as the r value corresponding to a top of the peak, and the distance $r_1$ between nearest neighbor particles is 1 to 2 times the average particle diameter $r_0$ of all spherical inorganic particles dispersed in the composite material; and Condition 2 where the radial distribution function graph has peaks among which a peak second closest to the origin provides a distance $r_2$ between second nearest neighbor particles as the r value corresponding to a top of the peak, and the radial distribution function g(r) has a local minimum value of 0.56 to 1.10 between the distance $r_1$ between nearest neighbor particles and the distance $r_2$ between second nearest neighbor particles.

2. The dental mill blank according to claim 1, wherein the radial distribution function g(r) is calculated from Formula (1): $g(r)=\{1/<\rho>\}\times\{dn/da\}$, wherein $<\rho>$ is an average density of the spherical inorganic particles in an observation plane that is an interior surface of the composite material, wherein the average density is determined from a scanning electron microscopy image of the interior surface of the composite material, dn is the number of spherical inorganic particles in a region between a circle with a circumference apart by the distance r from any spherical inorganic particle in the observation plane and a circle with a circumference apart by a distance of r+dr from the any spherical inorganic particle, and da is the area of the region, wherein $da=2\pi r\times dr$.

3. The dental mill blank according to claim 1, wherein a total amount of the group or groups of identical diameter spherical particles dispersed in the resin matrix is 10 parts by mass to 1,500 parts by mass based on 100 parts by mass of the resin matrix, and an amount of the group of superfine particles dispersed in the resin matrix is 0.1 parts by mass to 50 parts by mass based on 100 parts by mass of the resin matrix.

4. The dental mill blank according to claim 1, wherein all the group or groups of identical diameter spherical particles in the inorganic particles have an average primary particle diameter in a range of 230 nm to 1,000 nm, and the group of superfine particles has an average primary particle diameter in a range of 3 nm to 75 nm.

5. The dental mill blank according to claim 1, wherein a difference between $n_{(MX)}$ and $n_{(G\text{-}PIDm)}(n_{(G\text{-}PIDm)}-n_{(MX)})$, which is represented by $\Delta n$, is 0.001 to 0.1 for each $n_{(G\text{-}PIDm)}$.

6. The dental mill blank according to claim 1, wherein the at least one composite material in the milling target portion includes a plurality of composite materials having different compositions and being bonded together.

7. A method of producing the dental mill blank according to claim 1 having a milling target portion in a specific shape, the method comprising:

mixing a polymerizable monomer component (A), inorganic particles (B), and a polymerization initiator (C) to form a polymerizable curable composition, the polymerizable monomer component (A) being capable of forming a cured product having a refractive index of 1.40 to 1.57 for light with a wavelength of 589 nm at 25° C., the inorganic particles (B) comprising: the group of identical diameter spherical particles comprising a material having a refractive index higher than that of the cured product made from the polymerizable monomer component (A) for light with a wavelength of 589 nm at 25° C.; and the group of superfine particles; and subjecting the polymerizable curable composition to cast molding and polymerization to form a composite material bulk body that forms a whole or part of the milling target portion, wherein the mixing is carried out so as to form a polymerizable curable composition capable of forming a cured product containing spherical inorganic particles that form all the group or groups of identical diameter spherical particles and have a short-range order structure satisfying the Conditions 1 and 2 as an arrangement structure.

8. The method according to claim 7, wherein at least some of the group or groups of identical diameter spherical particles in the polymerizable curable composition are in the form of an organic-inorganic composite filler comprising: one group of identical diameter spherical particles; and a resin having a refractive index lower than that of spherical inorganic particles of the one group of identical diameter spherical particles for light with a wavelength of 589 nm at 25° C. and being free of any group of identical diameter spherical particles other than the one group of identical diameter spherical particles.

9. The method according to claim 7, wherein the polymerization initiator (C) is a thermal polymerization initiator, and the cast molding and polymerization are carried out at 60° C. to 200° C.

* * * * *